(12) United States Patent
Fabiilli et al.

(10) Patent No.: US 10,335,368 B2
(45) Date of Patent: Jul. 2, 2019

(54) ULTRASOUND-TRIGGERABLE AGENTS FOR TISSUE ENGINEERING

(71) Applicant: THE REGENTS OF THE UNIVERSITY OF MICHIGAN, Ann Arbor, MI (US)

(72) Inventors: Mario L. Fabiilli, Plymouth, MI (US); Christopher Wilson, Ann Arbor, MI (US); Frederic Padilla, Ann Arbor, MI (US); Francisco Martin-Saavedra, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/055,263

(22) Filed: Feb. 26, 2016

(65) Prior Publication Data
US 2016/0279059 A1    Sep. 29, 2016

Related U.S. Application Data

(62) Division of application No. 13/913,149, filed on Jun. 7, 2013, now abandoned.

(60) Provisional application No. 61/657,351, filed on Jun. 8, 2012.

(51) Int. Cl.
| | | |
|---|---|---|
| *A61K 9/00* | (2006.01) | |
| *A61K 35/00* | (2006.01) | |
| *A61K 38/18* | (2006.01) | |
| *A61K 38/36* | (2006.01) | |
| *A61K 41/00* | (2006.01) | |
| *A61K 47/06* | (2006.01) | |
| *A61K 47/10* | (2017.01) | |
| *A61K 47/24* | (2006.01) | |
| *A61K 9/107* | (2006.01) | |
| *A61K 9/113* | (2006.01) | |
| *A61L 27/22* | (2006.01) | |
| *A61L 27/38* | (2006.01) | |
| *A61L 27/52* | (2006.01) | |
| *A61L 27/54* | (2006.01) | |
| *A61L 27/56* | (2006.01) | |

(52) U.S. Cl.
CPC .......... *A61K 9/1075* (2013.01); *A61K 9/0009* (2013.01); *A61K 9/0014* (2013.01); *A61K 9/0024* (2013.01); *A61K 9/107* (2013.01); *A61K 9/113* (2013.01); *A61K 38/1825* (2013.01); *A61K 38/363* (2013.01); *A61K 41/0028* (2013.01); *A61K 47/06* (2013.01); *A61K 47/10* (2013.01); *A61K 47/24* (2013.01); *A61L 27/225* (2013.01); *A61L 27/227* (2013.01); *A61L 27/3804* (2013.01); *A61L 27/52* (2013.01); *A61L 27/54* (2013.01); *A61L 27/56* (2013.01); *A61K 35/00* (2013.01); *A61L 2300/252* (2013.01); *A61L 2300/414* (2013.01); *A61L 2300/418* (2013.01); *A61L 2300/62* (2013.01)

(58) Field of Classification Search
USPC ........................................................ 424/423
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,270,163 A | 12/1993 | Gold et al. |
| 5,367,066 A | 11/1994 | Urdea et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,637,459 A | 6/1997 | Burke et al. |
| 5,645,985 A | 7/1997 | Froehler et al. |
| 5,681,941 A | 10/1997 | Cook et al. |
| 5,750,692 A | 5/1998 | Cook et al. |
| 5,763,588 A | 6/1998 | Matteucci et al. |
| 5,830,653 A | 11/1998 | Froehler et al. |
| 5,840,276 A | 11/1998 | Apfel |
| 6,005,096 A | 12/1999 | Matteucci et al. |

(Continued)

FOREIGN PATENT DOCUMENTS

| | | |
|---|---|---|
| EP | 1072679 A2 | 1/2001 |
| WO | WO-1997/12896 A1 | 4/1997 |

(Continued)

OTHER PUBLICATIONS

Altland et al., Low-intensity ultrasound increases endothelial cell nitric oxide synthase activity and nitric oxide synthesis, *J. Thromb. Haemost.*, 2:637-43 (2004).

(Continued)

*Primary Examiner* — Devang K Thakor
(74) *Attorney, Agent, or Firm* — Marshall, Gerstein & Borun LLP

(57) ABSTRACT

The present invention is directed to compositions and methods for delivering a tissue scaffold comprising ultrasound-triggerable agents to an individual.

25 Claims, 16 Drawing Sheets

(56) References Cited

U.S. PATENT DOCUMENTS

| | | | |
|---|---|---|---|
| 7,223,833 | B1 | 5/2007 | Nielsen et al. |
| 7,611,728 | B2 | 11/2009 | Kidane et al. |
| 7,667,004 | B2 | 2/2010 | Zhong et al. |
| 2007/0071683 | A1 | 3/2007 | Dayton et al. |
| 2009/0214649 | A1 | 8/2009 | Gazit et al. |
| 2010/0178305 | A1 | 7/2010 | Rapoport et al. |
| 2011/0104258 | A1 | 5/2011 | Pit et al. |
| 2011/0306581 | A1* | 12/2011 | Rapoport ............ A61K 9/0026 514/171 |

FOREIGN PATENT DOCUMENTS

| | | |
|---|---|---|
| WO | WO-2005/051305 A2 | 6/2005 |
| WO | WO2010077671 * | 7/2010 |

OTHER PUBLICATIONS

Apfel et al., Gauging the likelihood of cavitation from short-pulse, low-duty cycle diagnostic ultrasound, *Ultrasound Med. Biol.*, 17:179-85 (1991).

Arima et al., Percutaneous radiofrequency ablation with transarterial embolization is useful for treatment of stage 1 renal cell carcinoma with surgical risk: results at 2-year mean follow up, *Int. J. Urol.*, 14(7):585-90 (2007).

Atchley et al., Thresholds for cavitation produced in water by pulsed ultrasound, *Ultrasonics*, 26:280-5 (1988).

Bale et al., Strain enhancement of elastic modulus in fine fibrin clots, *Thromb. Res.*, 52:565-72 (1988).

Cameron et al., The influence of substrate creep on mesenchymal stem cell behaviour and phenotype, *Biomaterials*, 32:5979-93 (2011).

Charbonnet et al., Treatment of gastrointestinal hemorrhage, *Abdom. Imaging*, 30(6):719-26 (2005).

Chen, Bubble Science, *Engineering and Technology*, 3(2):34-47 (2011).

Chin et al., Hydrogel-perfluorocarbon composite scaffold promotes oxygen transport to immobilized cells, *Biotechnology Progress*, 24(2):358-66 (2008).

Clausell-Tormos et al., Droplet-based microfluidic platforms for the encapsulation and screening of Mammalian cells and multicellular organisms, *Chemistry and Biology*, 15:427-37 (2008).

Cook, Medicinal chemistry of antisense oligonucleotides—future opportunities, *Anti-Cancer Drug Design*, 6:585-607 (1991).

Couture et al., In vivo targeted delivery of large payloads with an ultrasound clinical scanner, *Med. Phys.*, 39:5229-37 (2012).

Couture et al., Ultrasound internal tattooing, *Med. Phys.*, 38:1116-23 (2011).

Crawford et al., Peptide aptamers: tools for biology and drug discovery, *Brief. Funct. Genomic Proteomic*, 2(1):72-9 (2003).

Datta et al., Ultrasound-enhanced thrombolysis using Definity as a cavitation nucleation agent, *Ultrasound Med. Biol.*, 34(9):1421-33 (2008).

Dayton et al., Application of ultrasound to selectively localize nanodroplets for targeted imaging and therapy, *Mol. Imaging*, 5(3):160-174 (2006).

Dayton et al., Targeted imaging using ultrasound, *J. Magn. Reson. Imaging*, 16(4):362-77 (2002).

Dehghani et al., Engineering porous scaffolds using gas-based techniques, *Curr. Opin. Biotechnol.*, 22:661-6 (2011).

Diaz-Lopez et al., Liquid perfluorocarbons as contrast agents for ultrasonography and (19)F-MRI, *Pharm Res.*, 27(1):1-16 (2010).

Doan et al., In vitro effects of therapeutic ultrasound on cell proliferation, protein synthesis, and cytokine production by human fibroblasts, osteoblasts, and monocytes, *J. Oral Maxil. Surg.*, 57:409-19 (1999).

Eckstein (ed.). Oligonucleotides and Analogues, 1st Ed. Oxford University Press, New York, (1991).

Eisenbrey et al., Development and optimization of a doxorubicin loaded poly(lactic acid) contrast agent for ultrasound directed drug delivery, J. Control Release, 143(1):38-44 (2010).

Engler et al., Matrix elasticity directs stem cell lineage specification, Cell, 126:677-89 (2006).

Englisch et al., Angewandte Chemie, International Edition, 30:613-722 (1991).

Epstein-Barash et al., A microcomposite hydrogel for repeated on-demand ultrasound-triggered drug delivery, *Biomaterials*, 31:5208-17 (2010).

Fabiilli et al., Acoustic droplet-hydrogel composites for spatial and temporal control of growth factor delivery and scaffold stiffness, *Acta. Biomater.*, 9(7):7399-7409 (2013).

Fabiilli et al., Delivery of chlorambucil using an acoustically-triggered perfluoropentane emulsion, *Ultrasound Med. Biol.*, 36:1364-75 (2010).

Fabiilli et al., Delivery of water-soluble drugs using acoustically triggered perfluorocarbon double emulsions, *Pharm. Res.*, 27:2753-65 (2010).

Fabiilli et al., The role of inertial cavitation in acoustic droplet vaporization, *IEEE Trans. Ultrason. Ferroelectr. Freq. Control*, 56:1006-17 (2009).

Fang et al., A study of the formulation design of acoustically active liposheres as carriers for drug delivery, *Eur. J. Pharm. Biopharm.*, 67(1):67-75 (2007).

Fang et al., Acoustically active perfluorocarbon nanoemulsions as drug delivery carriers for camptothecin: drug release and cytotoxicity against cancer cells, *Ultrasonics*, 49(1):39-46 (2009).

Freier et al., The ups and downs of nucleic acid duplex stability: structure-stability studies on chemically-modified DNA RNA duplexes, *Nucleic Acids Research*, 25:4429-43 (1997).

Ganta et al., A review of stimuli-responsive nanocarriers for drug and gene delivery, *J. Control Release*, 126(3):187-204 (2008).

Garvin et al., Controlling the spatial organization of cells and extracellular matrix proteins in engineered tissues using ultrasound standing wave fields, *Ultrasound Med. Biol.*, 36:1919-32 (2010).

Ghajar et al., The effect of matrix density on the regulation of 3-D capillary morphogenesis, *Biophys. J.*, 94:1930-41 (2008).

Giesecke et al., Ultrasound-mediated cavitation thresholds of liquid perfluorocarbon droplets in vitro, *Ultrasound Med. Biol.*, 29(9):1359-65 (2003).

Hernot et al., Microbubbles in ultrasound-triggered drug and gene delivery, *Adv. Drug Deliv. Rev.*, 60(10):1153-66 (2008).

Hwang et al., Development and evaluation of perfluorocarbon nanobubbles for apomorphine delivery, *J. Pharm. Sci.*, 98(10):3735-47 (2009).

Ibsen et al., A novel nested liposome drug delivery vehicle capable of ultrasound triggered release of its payload, *J. Control Release*,155:358-66 (2011).

Katz, The reversible reaction of sodium thymonucleate and mercuric chloride, *J. Am. Chem. Soc.*, 74:2238 (1951).

Kawabata et al., "Nanoparticles with multiple perfluorocarbons for controllable ultrasonically induced phase shifting," *Jpn. J. Appl. Phys.*, 44(6B):4548-52 (2005).

Kopylov et al., Combinatorial chemistry of nucleic acids: SELEX, *Molec. Biol.*, 34(6):940-54 (2000).

Kosturko et al., The crystal and molecular structure of a 2:1 complex of 1-methylthymine-mercury (II), *Biochemistry*, 13:3949 (1974).

Kripfgans et al., Acoustic droplet vaporization for temporal and spatial control of tissue occlusion: a kidney study, *IEEE Trans. Ultrason. Ferroelectr. Freq. Control.*, 52(7):1101-10 (2005).

Kripfgans et al., Acoustic droplet vaporization for therapeutic and diagnostic applications, Ultrasound Med. Biol., 26(7):1177-89 (2000).

Kripfgans et al., In vivo droplet vaporization for occlusion therapy and phase aberration correction, *IEEE Trans. Ultrason. Ferroelectr. Freq. Control.*, 49:726-38 (2002).

Kripfgans et al., On the acoustic vaporization of micrometer-sized droplets, *J. Acoust. Soc. Am.*, 116:272-81 (2004).

Kroschwitz (ed.), Concise Encyclopedia of Polymer Science and Engineering, John Wiley & Sons, 858-9 (1990).

Laing et al., Ultrasound-mediated delivery of echogenic immunoliposomes to porcine vascular smooth muscle cells in vivo, *J. Liposome Res.*, 20(2):160-7 (2010).

(56) References Cited

OTHER PUBLICATIONS

Langer et al., Tissue engineering, *Science*, 260(5110):920-6 (1993).
Langer, New methods of drug delivery, *Science*, 249(4976):1527-33 (1990).
Lentacker et al., Design and evaluation of doxorubicin-containing microbubbles for ultrasound-triggered doxorubicin delivery: cytotoxicity and mechanisms involved, *Mol Ther.*, 18(1):101-8 (2010).
Liang et al., Sonoporation, drug delivery, and gene therapy, *Proc, Inst. Mech. Eng. H.*, 224(H2):343-61 (2010).
Lima et al., Microbubbles as biocompatible porogens for hydrogel scaffolds, *Acta. Biomater.*, 8(12):4334-41 (2012).
Lo et al., Spatial control of gas bubbles and their effects on acoustic fields, *Ultrasound Med. Biol.*, 32:95-106 (2006).
Maillard et al., Perfluorodecalin-enriched fibrin matrix for human islet culture, *Biomaterials*, 32:9282-9 (2011).
Malda et al., Oxygen gradients in tissue-engineered PEGT/PBT cartilaginous constructs: measurement and modeling, *Biotechnol. Bioeng.*, 86(1):9-18 (2004).
Marchioni et al., Structural changes induced in proteins by therapeutic ultrasounds, *Ultrasonics*, 49:569-76 (2009).
Mayer(ed.), Nucleic Acid and Peptide Aptamers: Methods and Protocols, Humana Press, (2009).
Nair et al., Novel polymeric scaffolds using protein microbubbles as porogen and growth factor carriers, *Tissue Eng. Part C Methods*, 16:23-32 (2010).
Osol (ed.), Remington's Pharmaceutical Sciences, 16th ed. (1980).
Petroianu, Arterial embolization for hemorrhage caused by hepatic arterial injury, *Dig. Dis. Sci.*, 52(10):2478-81 (2007).
Rapoport et al., Controlled and targeted tumor chemotherapy by ultrasound-activated nanoemulsions/microbubbles, *J. Control Release*, 138(3):268-76 (2009).
Rapoport, Physical stimuli-responsive polymeric micelles for anticancer drug delivery, *Prog Polym. Sci.*, 32(8):962-990 (2007).
Ren et al., A novel ultrasound microbubble carrying gene and Tat peptide: preparation and characterization, *Acad. Radiol.*, 16(12):1457-65 (2009).
Riess, Oxygen carriers ("blood substitutes")—raison d'etre, chemistry, and some physiology, *Chem. Rev.*, 101(9):2797-920 (2001).
Sahni et al., Binding of basic fibroblast growth factor to fibrinogen and fibrin, *J. Biol. Chem.*, 273:7554-9 (1998).
Sahni et al., FGF-2 binding to fibrin(ogen) is required for augmented angiogenesis, *Blood*, 107:126-31 (2006).
Sambrook et al., *Molecular Cloning: A Laboratory Manual*, 2nd ed. (1989).
Sanghvi, Chapter 15, Antisense Research and Applications, *CRC Press*, 289-302 (1993).
Shah et al., "Strain hardening of fibrin gels and plasma clots," Rheol Acta 36:262-8 (1997).
Sheeran et al., Decafluorobutane as a phase-change contrast agent for low-energy extravascular ultrasonic imaging, *Ultrasound Med. Biol.*, 37:1518-30 (2011).
Sommer et al., Interaction of heparin with human basic fibroblast growth factor: protection of the angiogenic protein from proteolytic degradation by a glycosaminoglycan, *J. Cell Physiol.*, 138:215-20 (1989).
Thomas, The interaction of $HgCl_2$ with sodium thymonucleate, *J. Am. Chem. Soc.*, 76:6032 (1954).
Tian et al., Effects of ultrasound and additives on the function and structure of trypsin, *Ultrasonics Sonochemistry*, 11:399-404 (2004).
Tinkov et al., Microbubbles as ultrasound triggered drug carriers, *J Pharm Sci.* 98(6):1935-61 (2009).
Tuerk et al., Systematic evolution of ligands by exponential enrichment: RNA ligands to bacteriophage T4 DNA polymerase, Science, 249:505-10 (1990).
Unger et al., Therapeutic applications of lipid-coated microbubbles, *Adv, Drug Deliv. Rev.*, 56(9):1291-314 (2004).
Wells et al., Medical ultrasound: imaging of soft tissue strain and elasticity, *J. R. Soc. Interface*, 8:1521-49 (2011).
Whang et al., Engineering bone regeneration with bioabsorbable scaffolds with novel microarchitecture, *Tissue Engineering*, 5:35-51 (1999).
Wu et al., Advanced hepatocellular carcinoma: treatment with high-intensity focused ultrasound ablation combined with transcatheter arterial embolization, *Radiology*. 235(2):659-67 (2005).
Yamane, et al., Aptamers and aptamer targeted delivery, *J. Am. Chem. Soc.*, 83:2599 (1961).
Yan et al., Aptamers and aptamer targeted delivery, RNA Biol., 6(3):316-20 (2009).
Yang et al., Effect of ultrasound contrast agent dose on the duration of focused-ultrasound-induced blood-brain barrier disruption, *J. Acoust. Soc. Am.*, 126(6):3344-9 (2009).
Zhang, et al., An extremely stable and orthogonal DNA base pair with a simplified three-carbon backbone, *J. Am. Chem. Soc.*, 127:74-5 (2005).
Zhang et al., Initial investigation of acoustic droplet vaporization for occlusion in canine kidney, *Ultrasound Med. Biol.*, 36(10):1691-703 (2010).
Zimmermann et al., A novel silver(i)-mediated DNA base pair, *J. Am. Chem. Soc.*, 124:13684-5 (2002).
International Search Report and Written Opinion of the International Search Authority, European Patent Office, PCT/US2013044817, dated Aug. 30, 2013.
Montesano, et al. "Transforming growth factor β stimulates collagen-matrix contraction by fibroblasts: Implications for wound healing," Proc. Natl. Acad. Sci. USA 85:4894-4897 (1988).
Lee, et al. "CTGF directs fibroblast differentiation from human mesenchymal stem/stromal cells and defines connective tissue healing in a rodent injury model," J Clin Invest 129(9):3340-3349 (2010).

* cited by examiner

ULTRASOUND-TRIGGERABLE AGENTS FOR TISSUE ENGINEERING

CROSS REFERENCE TO RELATED APPLICATIONS

This application is a Divisional of U.S. application Ser. No. 13/913,149, filed Jun. 7, 2013, which claims the priority benefit under 35 U.S.C. § 119(e) of U.S. Provisional Application No. 61/657,351, filed Jun. 8, 2012, the disclosures of which are incorporated herein by reference in their entirety.

STATEMENT OF GOVERNMENT INTEREST

This invention was made with government support under DE013386 awarded by the National Institutes of Health and W81XWH-10-1-0992 awarded by the Army Medical Research and Materiel Command. The government has certain rights in the invention.

FIELD OF THE INVENTION

The present invention is directed to compositions and methods for delivering a tissue scaffold comprising ultrasound-triggerable agents to an individual.

BACKGROUND OF THE INVENTION

Particles that release a therapeutic payload upon interaction with an internal stimulus, such as pH or hypoxia, or the application of an externally-applied stimulus, such as heat or ultrasound (US), are being studied in an effort to localize drug delivery to target areas [Dayton et al., Mol Imaging. 5(3): 160-174 (2006); Ganta et al., J Control Release. 126(3): 187-204 (2008); Laing et al., J Liposome Res. 20(2): 160-167 (2010); Rapoport, Prog Polym Sci. 32(8): 962-990 (2007); Unger et al., Adv Drug Deliv Rev. 56(9):1291-1314 (2004)]. The control of localized delivery is especially important for drugs that possess narrow therapeutic windows, thereby minimizing systemic side-effects. The interaction of US with payload-containing particles can generate acoustic cavitation, heating, radiation forces, and sonoporation. The last effect, the transient increase in cell membrane permeability, can greatly enhance the uptake of drugs, genes, and peptides encapsulated within US-activated particles [Eisenbrey et al., J Control Release. 143(1): 38-44 (2010); Lentacker et al., Mol Ther. 18(1): 101-108 (2010); Liang et al., Proc Inst Mech Eng H. 224(H2): 343-361 (2010); Ren et al., Acad Radiol. 16(12):1457-1465 (2009)]. These particle-US interactions can also produce therapeutic effects to be utilized in diverse applications such as thrombolysis [Datta et al., Ultrasound Med Biol. 34(9): 1421-1433 (2008)] or in the reversible disruption of the blood-brain barrier [Yang et al., J Acoust Soc Am. 126(6): 3344-3349 (2009)].

Colloidal particles utilized in US-mediated drug release are typically shell-stabilized microbubbles or droplets containing, respectively, perfluorocarbon (PFC) gases or liquids. The former colloids evolved from clinically-utilized US contrast agents, which are micron-sized gas bubbles that increase the echogenicity in perfused tissue upon intravenous administration. Due to their size, the microbubbles are transpulmonary and resonant at frequencies utilized in clinical imaging systems [Dayton et al., J Magn Reson Imaging. 16(4): 362-377 (2002)]. Therapeutic agents are typically incorporated into the microbubbles using one of the following methods: attachment to or intercalation within the shell; complexation of secondary carriers to the microbubble shell; or incorporation within a fluid inside the shell [Hernot et al., Adv Drug Deliv Rev. 60(10): 1153-1166 (2008); Tinkov S, Bekeredjian R, Winter G, Coester C. Microbubbles as ultrasound triggered drug carriers. J Pharm Sci. 98(6):1935-1961 (2009)].

As highlighted in a recent review [Diaz-Lopez et al., Pharm Res. 27(1): 1-16 (2010)], PFC emulsions have also been studied as US contrast agents and drug delivery systems due to their increased stability, longer circulation times, and ability to extravasate if formulated as nanoparticles. Due to the hydrophobicity and lipophobicity of the dispersed PFC phase [Riess, Chem Rev. 101(9): 2797-2919 (2000)], therapeutic agents are typically loaded into the emulsion using similar techniques as those mentioned for microbubble delivery systems. One commonly utilized method is the use of an oil-phase, containing the therapeutic agent, co-emulsified with the PFC phase during formulation [Fabiilli et al., Ultrasound Med Biol. 36(8): 1364-1375 (2010); Fang et al., Eur J Pharm Biopharm. 67(1): 67-75 (2007); Fang et al., Ultrasonics. 49(1): 39-46 (2009); Hwang et al., J Pharm Sci. 98(10): 3735-3747 (2009)]. PFC emulsions, with or without a therapeutic payload, can be vaporized into gas bubbles using US, a mechanism termed acoustic droplet vaporization (ADV) [U.S. Pat. No. 5,840,276; Giesecke et al., Ultrasound in Medicine and Biology. 29(9): 1359-1365 (2003); Kripfgans et al., Ultrasound Med Biol. 26(7): 1177-1189 (2000); Kawabata et al., Jpn J Appl Phys. 44(6B): 4548-4552 (2005); Rapoport et al., J Control Release. 138(3): 268-276 (2009)]. ADV is a phenomenon whereby vaporization occurs only if the emulsion is exposed to acoustic amplitudes greater than a threshold value. PFCs used in emulsions suitable for ADV applications typically possess bulk boiling points that are lower than normal body temperature (37° C.), such as perfluoropentane (29° C. boiling point). Upon injection in vivo, the emulsions do not spontaneously vaporize due to the increased internal (i.e., Laplace) pressure, and hence boiling point elevation, of the PFC when formulated as droplets [Rapoport et al., J Control Release. 138(3): 268-276 (2009)]. Low boiling point PFCs, such as perfluoropentane, also enable the use of lower acoustic amplitudes to generate ADV [Fabiilli et al., Ultrasound Med Biol. 36(8): 1364-1375 (2010)] and the production of stable gas bubbles in vivo [Kripfgans et al., IEEE Trans Ultrason Ferroelectr Freq Control. 49(2): 726-738 (2002); Kripfgans et al., IEEE Trans Ultrason Ferroelectr Freq Control. 52(7): 1101-1110 (2005); Zhang et al., Ultrasound Med Biol. 36(10): 1691-703 (2010)]. The ADV of PFC emulsions containing a lipophilic, therapeutic payload can be used to facilitate the delivery and release of the therapeutic agent, as demonstrated with in vitro [Fabiilli et al., Ultrasound Med Biol. 36(8): 1364-1375 (2010); Fang et al., Eur J Pharm Biopharm. 67(1): 67-75 (2007); Fang et al., Ultrasonics. 49(1): 39-46 (2009); Hwang et al., J Pharm Sci. 98(10): 3735-3747 (2009)] and in vivo [Rapoport et al., J Control Release. 138(3): 268-276 (2009)] studies.

The ADV of micron-sized PFC emulsions, administered intravenously or intraarterially, has also been used to generate localized, vascular occlusion in vivo [Kripfgans et al., IEEE Trans Ultrason Ferroelectr Freq Control. 49(2): 726-738 (2002); Kripfgans et al., IEEE Trans Ultrason Ferroelectr Freq Control. 52(7): 1101-1110 (2005); Zhang et al., Ultrasound Med Biol. 36(10): 1691-703 (2010)]. The temporal duration of an ADV-generated occlusion is transient, especially for gas emboli generated from intravenously administered emulsions [Zhang et al., Ultrasound Med Biol. 36(10): 1691-703 (2010)]. Therefore, the ability to extend this duration may be therapeutically beneficial for surgical applications that require longer occlusion times such as radiofrequency ablation [Arima et al., Int J Urol. 14(7): 585-590 (2007)] and high intensity focused US thermal therapy [Wu et al., Radiology. 235(2): 659-667 (2005)]. ADV-generated occlusion could also be potentially used to treat hemorrhaging associated with vascular damage or other internal bleeding, which are currently treated using transcatheter embolization [Charbonnet et al., Abdom Imaging. 30(6): 719-726 (2005); Petroianu, Dig Dis Sci. 52(10): 2478-2481 (2007)].

More recent work showed that PFC emulsions can serve as carriers for water-soluble therapeutic agents. The emulsions could be vaporized using US, thereby releasing the encapsulated agent from the emulsions via ADV [Fabiilli et al., Pharm Res. 27(12): 2753-2765 (2010)].

SUMMARY OF THE INVENTION

Tissue engineering, the development of biological substitutes that can facilitate the regeneration of impaired or injured tissues, can potentially overcome limitations related to conventional surgical reconstruction and organ transplantation [Langer et al., Science 260(5110): 920-6 (1993)]. Scaffolds are frequently used in tissue regeneration as an adhesive substrate for the attachment of cells and/or encapsulation of inductive proteins (e.g., growth factors). Scaffolds are often fabricated with porous structures and composed of biodegradable materials. Porous scaffolds are favorable for cell survival, proliferation, and secretion of extracellular matrix components [Chen, Bubble Science, Engineering and Technology. 3(2): 34-47 (2011); Dehghani et al., Current Opinion in Biotechnology. 22:661-6 (2011)], and degradable materials afford controlled release of encapsulated proteins. While some success has been achieved with these technologies, most platforms that combine scaffolds with cells and/or bioactive factors provide no means of actively controlling the structure of the scaffold or the release of encapsulated factors. The present disclosure addresses at least three limitations of current engineered tissue scaffolds. First, tissue scaffold porosity can be actively and non-invasively regulated for pre- or post-implanted tissue scaffolds. Second, cellular growth and differentiation within the scaffolds, either pre- or post-implantation, can be non-invasively controlled by the localized release of biological agents with the scaffold [Langer, Science 249(4976): 1527-33 (1990)]. Third, the delivery of oxygen to cells that are deeply located within the scaffold increases cell viability by preventing localized hypoxia [Malda et al., Biotechnol Bioeng. 86(1): 9-18 (2004)].

Accordingly, the disclosure provides a device comprising (a) a tissue scaffold, (b) an emulsion that comprises a perfluorocarbon (PFC) droplet comprising a therapeutic agent in the interior thereof, the PFC having a mean droplet diameter that is at least about 20 micrometers (μm), and the emulsion having a volume fraction in the tissue scaffold of at least about 1% volume:volume.

The disclosure further provides a device comprising (a) a tissue scaffold, and (b) an emulsion comprising a first population of perfluorocarbon (PFC) droplets comprising a therapeutic agent in the interior thereof, said first population of PFC droplets having the property of vaporizing at a first ultrasound frequency and/or acoustic pressure threshold. In an embodiment, the device further comprises a second population of PFC droplets, said second population of PFC droplets having the property of vaporizing at a second ultrasound frequency and/or acoustic pressure threshold that is different than the first ultrasound frequency and/or acoustic pressure threshold.

In another aspect, a device is provided comprising: (a) a tissue scaffold; and (b) an emulsion comprising a population of perfluorocarbon (PFC) droplets comprising a therapeutic agent in the interior thereof, said population of PFC droplets comprising a first subpopulation of PFC droplets with a first mean droplet diameter and a second subpopulation of PFC droplets with a second mean droplet diameter; said first subpopulation of PFC droplets having the property of vaporizing at a first ultrasound frequency and/or acoustic pressure threshold, and said second subpopulation of PFC droplets having the property of vaporizing at a second ultrasound frequency and/or acoustic pressure threshold. In some embodiments, said first ultrasound frequency and/or acoustic pressure threshold and said second ultrasound frequency and/or acoustic pressure threshold are different.

In some embodiments, the device further comprises a progenitor cell. In related embodiments, the progenitor cell is a fibroblast, a chondrocyte, an osteoblast, a skeletal myocyte, a cardiac myocyte, a mesenchymal progenitor cell, a hematopoietic progenitor cell, a satellite cell, a neural progenitor cell, a pancreatic progenitor cell, a blast cell or a combination thereof.

In further embodiments, the emulsion is a double emulsion comprising a primary emulsion and a secondary emulsion. The primary emulsion, in various embodiments, comprises water-in-PFC. In yet further embodiments, the secondary emulsion comprises water-in-PFC-in-water. In additional embodiments, the emulsion comprises an oil-in-PFC-in-water emulsion.

The disclosure also provides embodiments wherein the device further comprises a surfactant. In related embodiments, a first surfactant stabilizing the primary emulsion is a triblock copolymer, and a second surfactant stabilizing the secondary emulsion is an aqueous soluble surfactant. The triblock copolymer, in some embodiments, comprises a perfluoroether and polyethylene glycol. In further embodiments, the aqueous soluble surfactant is selected from the group consisting of a protein, a lipid, an ionic copolymer and a non-ionic copolymer.

The disclosure additionally provides devices wherein initial pore size of the tissue scaffold is at least about 100 nanometers (nm). In some embodiments, vaporization of the PFC droplet results in a final pore size of the tissue scaffold of at least about 40 μm and up to about 5 millimeters (mm). In further embodiments, vaporization of the PFC droplet results in a stiffness of the tissue scaffold that is from about 0.05 kilopascal (kPa) to about 2 kPa.

Further embodiments of the disclosure provide a device wherein the density of the tissue scaffold is between about 100 μg/mL to about 100 mg/mL fibrinogen. In additional embodiments, the tissue scaffold comprises collagen.

In various embodiments of the disclosure, the device is implantable, while in further embodiments the device is topical.

With respect to the therapeutic agent, the disclosure provides embodiments wherein the therapeutic agent is selected from the group consisting of a polypeptide, a peptide, a polynucleotide, a viral particle, a gas, a contrast agent, a carbohydrate, an aminoglycoside and a small molecule. In some embodiments, the release of the therapeutic agent is controlled spatially, and in further embodiments the release of the therapeutic agent is controlled temporally.

In another aspect of the disclosure, a method of delivering an effective amount of a therapeutic agent to an individual in need thereof is provided, comprising administering a device of the disclosure to the individual.

DETAILED DESCRIPTION

Figure 1:
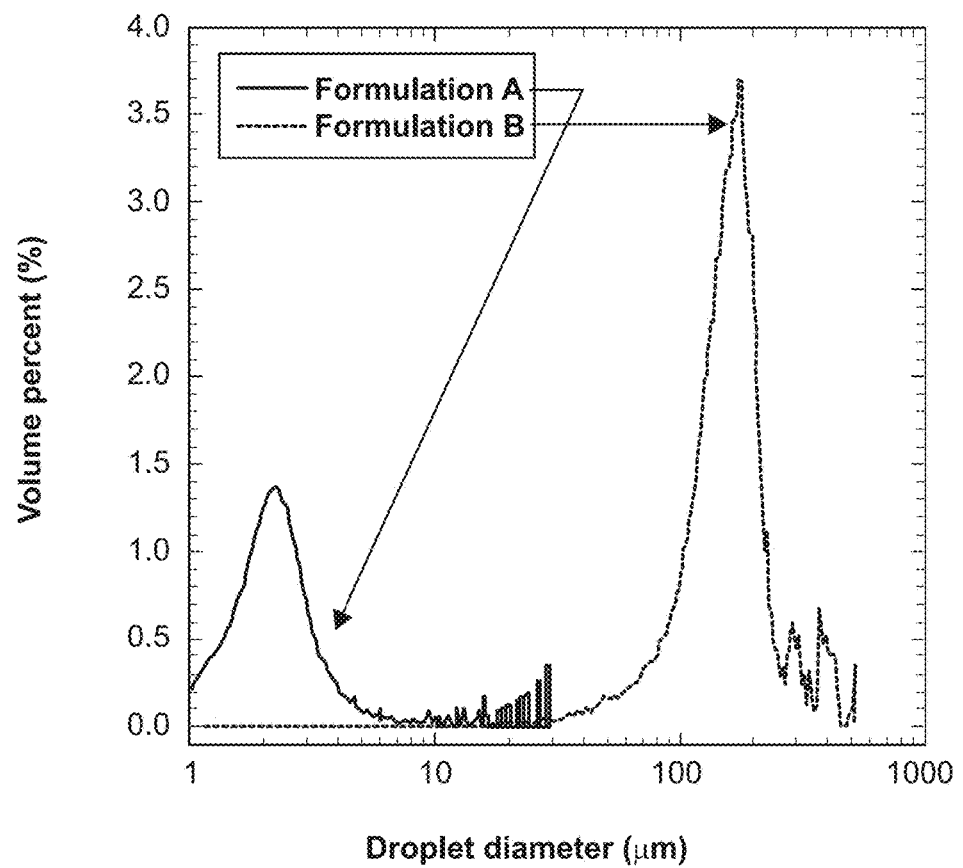
FIG. 1 depicts the volume-normalized size distributions of two double emulsion formulations. Formulation A had a distribution similar to other PFC emulsions administered intravascularly, with the majority of the droplet volume in particles less than 10 µm in diameter. The majority of droplet volume in Formulation B was in particles whose diameters are greater than 100 µm in diameter.

Sonosensitive emulsions and microbubbles have been studied extensively in the fields of diagnostic and therapeutic ultrasound, typically for contrast-enhanced imaging, intravascular delivery, and applications in cancer treatment [Diaz-Lopez et al., Pharmaceutical Research 27: 1-16 (2010); Tinkov et al., Journal of Pharmaceutical Sciences 98: 1935-61 (2009); Ibsen et al., Journal of controlled release: official journal of the Controlled Release Society 155: 358-66 (2011)]. The potential for these vehicles to be applied in tissue regeneration is relatively unexplored. Microbubbles have been used as porogens [Nair et al., Tissue Eng Part C-Me 16: 23-32 (2010); Lima et al., Acta Biomater 8(12): 4334-41 (2012)] and carriers of growth factors [Couture et al., Med Phys 38: 1116-23 (2011)] in the fabrication of scaffolds for tissue engineering, although the functions of microbubbles in these applications did not involve exposure to ultrasound. Liposome-microbubble-hydrogel composites treated with low frequency (20 kHz) ultrasound exhibited cavitation-based release of a model payload from the liposomes and afforded impressive control of release kinetics [Epstein-Barash et al., Biomaterials 31: 5208-17 (2010)], but it is unclear how the cavitation required for release will affect the bioactivity of a therapeutic payload or the viability of invading cells. In addition, the use of low frequency ultrasound limits the spatial resolution of the release. Previously, it has been shown that ultrasound in the range of 1-10 MHz can enhance the release of a protein-based therapeutic (thrombin) from a PFC double emulsion for intravascular delivery [Fabiilli et al., Pharm Res 27: 2753-65 (2010)]. Similar PFC emulsions, without a therapeutic payload, are well-tolerated in the circulation of large animal models at doses up to approximately $10^8$ droplets/kg [Zhang et al., Ultrasound Med Biol 36: 1691-703 (2010)]. Since megahertz frequency ultrasound is used to trigger ADV, release of a therapeutic payload can be localized to a volume on the order of cubic millimeters. The present disclosure provides composite materials that incorporate sonosensitive droplets, loaded with a therapeutic agent, in a biodegradable hydrogel scaffold. The disclosure also demonstrates selective, ultrasound-induced release of the therapeutic agent and alteration of scaffold properties.

Provided herein are devices that comprise a tissue scaffold and are designed for use in regenerative therapies. The scaffold in the device is able to provide a substrate for cell adhesion and/or new tissue formation. The device additionally comprises an emulsion which comprises a perfluorocarbon (PFC) droplet, and the PFC droplet is formulated to contain a therapeutic agent. The emulsion provides a means of actively controlling the structure of the scaffold and/or the release of the therapeutic agent(s). Thus, the present disclosure provides devices comprising a tissue scaffold and a PFC droplet and methods directed to their use in various tissue-based therapies.

The devices disclosed herein are also highly tunable, meaning that many aspects of the design and use of the device may be adjusted to affect the functioning of the device. These aspects include, but are not limited to, the tissue scaffold, the emulsion, the use of ultrasound and the therapeutic agent(s). Each of these aspects is described in detail below.

It is noted here that, as used in this specification and the appended claims, the singular forms "a," "an," and "the" include plural reference unless the context clearly dictates otherwise.

Tissue Scaffold

The device disclosed herein may be formulated as an in situ-polymerizable, porous, biodegradable tissue scaffold that further comprises a PFC emulsion. The tissue scaffold provides a substrate for cell adhesion, and comprises several aspects that allow for direct control over the structure and properties of the device. These aspects include, but are not limited to, the density, pore size and composition of the scaffold.

It will be appreciated that the various features of the devices disclosed herein, in various embodiments, act in concert. For example and without limitation, vaporization of a population of PFC droplets in a specific subvolume of the tissue scaffold results in a structural modification of the tissue scaffold (i.e., a change in pore size/porosity) in that same subvolume, which in turn results in enhanced invasion of host cells in the subvolume of the scaffold.

As used herein "tissue scaffold," "scaffold" and "hydrogel scaffold" are used interchangeably.

Composition

The composition of the tissue scaffold may be determined by those of ordinary skill in the art. Methods of making tissue scaffolds are described in Gazit et al., U.S. Patent Application Publication Number 20090214649, which is incorporated by reference herein in its entirety.

Tissue scaffolds for use in the devices and methods disclosed herein are comprised, in some embodiments, of proteins. For example and without limitation, the tissue scaffold is produced using fibrinogen and thrombin. In additional embodiments, the disclosure contemplates use of self-assembling peptide-based hydrogels, gelatin hydrogels, elastin and elastin-like hydrogels, collagen hydrogels, polysaccharide-based hydrogels (including but not limited to methylcellulose, agarose, alginate, and hyaluronic acid), composite hydrogels (including but not limited to collagen+fibrin blends, collagen+glycosaminoglycan blends, blends of the above and below), and synthetic hydrogels (including but not limited to polyethylene glycol, polyethylene glycol-fibrinogen conjugates, oligo(poly(ethylene glycol)-fumarate) derivatives, polyvinyl alcohol, and other hydrogels. Specific embodiments of the composition of tissue scaffolds contemplated by the disclosure are exemplified herein below.

In further embodiments, the tissue scaffold further comprises a progenitor cell. The progenitor cell, in various embodiments, is a fibroblast, chondrocyte, osteoblast, skeletal myocyte, cardiac myocyte, mesenchymal progenitor cell, an adipocyte progenitor cell, hematopoietic progenitor cell, satellite cell, neural progenitor cell, pancreatic progenitor cell, blast cell, a lymphoid progenitor cell, a myeloid progenitor cell, an endothelial progenitor cell, an epithelial progenitor cell, a renal progenitor cell, a retinal progenitor cell or a combination thereof. In further embodiments, the tissue scaffold comprises a population of progenitor cells.

In some embodiments, the relative amounts of fibrinogen and thrombin used for polymerizing the tissue scaffold control the rate of polymerization of the scaffold. For example and without limitation, a more rapid polymerization (less than about one minute) of the scaffold may be desired when the device is used subcutaneously when the amount of a therapeutic agent is to be concentrated in a specific tissue/region of the body. In this way, diffusion of the device is limited. For a more widespread distribution of the device, a slower polymerization (about one to several minutes or more) of the tissue scaffold may be desired. The relative rates of polymerization can be empirically determined by one of skill in the art.

Density

The density of the tissue scaffold refers to the concentration of protein dissolved in a solvent, wherein the protein is capable of polymerizing to form the scaffold. In general, a higher density scaffold leads to a longer term stability of the PFC droplets within the hydrogel scaffold. This is because a higher density scaffold provides viscous resistance to the vaporization of the PFC droplets within the scaffold. Therefore, a higher acoustic pressure is required to vaporize droplets within a higher density scaffold than a lower density scaffold. Thus, varying the density of the scaffold provides a level of control over the release of the therapeutic agent contained within the PFC droplet. It is contemplated that, in some embodiments, a slower release (e.g., over the course of days or weeks) rather than a fast release (e.g., over the course of hours or minutes) of the therapeutic agent is desired. In these embodiments, one method of effecting the slower release of the therapeutic agent comprises formulating the tissue scaffold at a higher density. Ultrasound-bubble interactions are more pronounced at lower scaffold densities than at higher scaffold densities due to the viscous resistance of the scaffold. Therefore, effects derived from ultrasound-bubble interactions such as mechanical stimulation of cells or sonoporation of cells are more pronounced at lower scaffold densities.

The disclosure therefore contemplates the use of various densities of protein within the hydrogel scaffold. According to the disclosure, the density of protein within the tissue scaffold is at least about 100 μg/mL and up to about 100 mg/mL or more. In some embodiments, the density of the protein within the tissue scaffold is from about 100 μg/mL to about 90 mg/mL, or from about 100 μg/mL to about 80 mg/mL, or from about 100 μg/mL to about 70 mg/mL, or from about 100 μg/mL to about 60 mg/mL, or from about 100 μg/mL to about 50 mg/mL, or from about 100 μg/mL to about 40 mg/mL, or from about 100 μg/mL to about 30 mg/mL, or from about 100 μg/mL to about 20 mg/mL, or from about 100 μg/mL to about 10 mg/mL or from about 100 μg/mL to about 1 mg/mL. In various embodiments, the density of the protein within the tissue scaffold is from about 1 mg/mL to about 100 mg/mL, or from about 1 mg/mL to about 50 mg/mL, or from about 1 mg/mL to about 40 mg/mL, or from about 1 mg/mL to about 30 mg/mL, or from about 1 mg/mL to about 20 mg/mL, or from about 1 mg/mL to about 10 mg/mL. In further embodiments, the density of the protein within the tissue scaffold is from about 1 mg/mL and up to about 5 mg/mL, about 10 mg/mL, about 15 mg/mL or about 20 mg/mL or more. Further embodiments contemplated include those wherein the density of the protein within the tissue scaffold is from about 1 mg/mL, from about 5 mg/mL, from about 10 mg/mL, from about 15 mg/mL, from about 20 mg/mL, from about 25 mg/mL, from about 30 mg/mL, from about 35 mg/mL, from about 40 mg/mL or from about 45 mg/mL up to about 50 mg/mL. In specific embodiments, the density of the protein within the tissue scaffold is about 100 μg/mL, 150 μg/mL, 200 μg/mL, 250 μg/mL, 300 μg/mL, 350 μg/mL, 400 μg/mL, 450 μg/mL, 500 μg/mL, 550 μg/mL, 600 μg/mL, 650 μg/mL, 700 μg/mL, 750 μg/mL, 800 μg/mL, 850 μg/mL, 900 μg/mL, 950 μg/mL, 1 mg/mL, about 2 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL or about 50 mg/mL. Indeed, the disclosure contemplates the use any density between 1 mg/mL and 50 mg/mL, inclusive.

Porosity/Pore Size and Stiffness/Dissipation

The porosity and pore size of the tissue scaffold are additional aspects that afford the ability to control aspects of the properties of the device. Porosity refers to the volume fraction of open space within a tissue scaffold (typically reported as a percentage) and can be determined by microscopic methods or through permeation experiments. Porosity, along with pore size (a characteristic dimension of the open structure(s) within the scaffold) and pore interconnectivity contribute to the resistance to fluid flow, molecular diffusion, and cellular invasion of a tissue scaffold. Most hydrogels are highly porous with porosities of that can be in excess of 99% (i.e., 99% by volume open space, 1% by volume solid material) but the pore sizes are quite small, in the range of 500 nm to 15 μm diameter pores. These pores are small enough to limit migration of cells and diffusion of one or more therapeutic agents into (or out of) the scaffold. The porosity and pore size of hydrogel scaffolds are generally dependent on polymerization conditions including but not limited to the concentration of scaffold precursors (for example, and without limitation, synthetic or biological polymers, enzymes, cross linking agents, and buffer systems), temperature, and atmosphere used during preparation of the scaffold.

The porosity of the scaffold may be adjusted, however, through increasing the pore size of the scaffold, which is effected via vaporization (i.e., Acoustic Droplet Vaporization (ADV)) of the PFC droplets within the scaffold. ADV increases gel porosity due to the phase-transitioning of the PFC liquid into a gas. PFC droplet vaporization results in an increase in scaffold pore size, which ultimately results in an increase in porosity.

Adjusting the porosity of the scaffold, and thus the amount of fluid and number of cells that are able to pass through the scaffold, allows for the ability to control the relative rate of degradation of the scaffold. As discussed above, a higher porosity results in more fluid penetrating into the scaffold and increased cellular in-growth, which in turn will lead to a faster degradation of the scaffold. A lower porosity, on the other hand, results in less fluid passing through the scaffold and less cellular in-growth, which leads to a slower degradation of the scaffold.

In addition, while in some embodiments the porosity of the scaffold is high prior to PFC droplet vaporization, the pore size in these embodiments is small. Therefore, while fluid is able to pass through the scaffold, cells cannot readily pass through. In these embodiments, the increase in pore size resulting from PFC droplet vaporization further allows cells to infiltrate the scaffold more easily. Thus, cells that are required for tissue regeneration are able to enter the scaffold and perform their functions.

Cells that are able to enter the scaffold, in some embodiments, are recruited to the site by factors released from the PFC droplets.

The disclosure contemplates that in one embodiment the initial (i.e., prior to PFC droplet vaporization) pore size of the polymerized scaffold is, on average, about 100 nanometers (nm). In further embodiments, the initial pore size is at least about 100 nm to about 10 μm, or at least about 100 nm to about 5 μm, or at least about 100 nm to about 2 μm, or at least about 100 nm to about 900 nm, or at least about 100 nm to about 800 nm, or at least about 100 nm to about 700 nm, or at least about 100 nm to about 600 nm, or at least about 100 nm to about 500 nm, or at least about 100 nm to about 400 nm, or at least about 100 nm to about 300 nm, or at least about 100 nm to about 200 nm. In specific embodiments, the initial pore size of the polymerized scaffold is at least about 100 nm, 200 nm, 300 nm, 400 nm, 500 nm, 600 nm, 700 nm, 800 nm, 900 nm, 950 nm, 1000 nm, 2 µm, 5 µm, 7 µm, 10 µm or more.

As discussed above, scaffold pore size is increased by PFC droplet vaporization. Thus, the disclosure also contemplates that, in one embodiment, the final (i.e., after PFC droplet vaporization) pore size of the polymerized scaffold is about 40 µm. In further embodiments, the final pore size is at least about 1 µm and up to about 50 µm, or at least about 5 µm and up to about 40 µm, or at least about 40 µm and up to about 5 millimeters (mm), or at least about 40 µm and up to about 4 mm, or at least about 40 µm and up to about 3 mm, or at least about 40 µm and up to about 2 mm, or at least about 40 µm and up to about 1 mm, or at least about 100 µm and up to about 5 mm, or at least about 100 µm and up to about 4 mm, or at least about 100 µm and up to about 3 mm, or at least about 100 µm and up to about 2 mm, or at least about 100 µm and up to about 1 mm, or at least about 100 µm and up to about 900 µm, or at least about 100 µm and up to about 800 µm, or at least about 100 µm and up to about 500 µm m. In additional embodiments, the final pore size is at least about 200 µm and up to about 1 mm, or at least about 500 µm and up to about 1 mm, or at least about 200 µm and up to about 800 µm, or at least about 500 µm and up to about 2 mm. In specific embodiments, the final pore size of the polymerized scaffold is at least about 1 µm, 5 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 2 mm, 3 mm, 4 mm, 5 mm or more.

Another way of describing the initial versus the final pore size of the polymerized scaffold is by percent volume increase of the tissue scaffold. Accordingly, the disclosure provides devices in which, following vaporization, the tissue scaffold increase by about 1% up to about 30% or more, or by about 5% up to about 30%, or by about 10% up to about 30% or more in volume.

Mechanical properties such as scaffold stiffness and viscoelasticity can also be modulated via ADV. Viscoelasticity is defined in terms of the dissipation factor, which is the tangent of the phase angle δ. As exemplified herein, ADV results in modulation of the stiffness of acoustic droplet-fibrin composites. In general, ADV causes an increase in shear stiffness of a scaffold, which is also a general indicator of the viscoelasticity of the scaffold. Higher viscoelasticity is indicative of a more dissipative mechanical response. Modulation of properties such as pore size and stiffness/viscoelasticity are useful in tailoring the function of the scaffold. Accordingly, methods of controlling and/or modulating the porosity and/or pore size of a tissue scaffold are provided by the disclosure, and comprise the step of exposing all or a portion of the tissue scaffold to ultrasound. In this way, the porosity and/or pore size and/or stiffness/viscoelasticity of the tissue scaffold is modulated in a global or localized manner. Local increases (i.e., an increase in at least one region or subvolume of the scaffold versus the entirety of the scaffold) in pore size and/or stiffness, in various embodiments, will allow the infiltration of cells and/or fluid into the scaffold, where they proliferate and differentiate. The local or global shifts in pore structure and/or stiffness also provide, in some embodiments, specific topographical cues that promote differentiation of encapsulated or invading cells along various lineages (for example and without limitation, endothelial or osteogenic). For example, Engler et al. [Cell 126: 677-689 (2006)] described how mesenchymal stem cell (MSC) differentiation can be influenced by the stiffness of a scaffold. Specifically, Engler et al. [Cell 126: 677-689 (2006)] described how MSCs display neurogenic, myogenic, or osteogenic characteristics when grown on scaffolds with stiffnesses in the range of 0.1-1 kPa, 8-17 kPa, and 25-40 kPa, respectively. Thus, in some embodiments, the disclosure contemplates that vaporization of the PFC droplet results in a stiffness of the tissue scaffold that is from about 0.05 kilopascal (kPa) to about 40 kPa, or from about 0.1 kPa to about 1 kPa, or from about 1 kPa to about 17 kPa, or from about 20 kPa to about 40 kPa, or from about 0.05 kPa to about 5 kPa, or from about 0.05 kPa to about 2 kPa. In further embodiments, the proliferation and/or differentiation of the cells is enhanced by the release of one or more therapeutic agents from a PFC droplet.

Emulsion

The devices disclosed herein comprise an emulsion, and the emulsion further comprise PFC droplets. Specifically, and in various embodiments, the present disclosure contemplates the use of double emulsions. Double emulsions comprising PFC droplets are known in the art, and are described in Fabiilli et al., Pharm Res. 27(12): 2753-2765 (2010), the disclosure of which is incorporated by reference herein in its entirety. In further embodiments, a single emulsion (PFC-in-water) that contains one or more therapeutic agents conjugated to the droplet surface is used. In these embodiments, the amount of therapeutic agent that can be loaded into the emulsion is less than what can be loaded using a double emulsion. Therefore, in some embodiments, a higher droplet concentration is used.

A double emulsion comprises a primary (water-in-PFC) and a secondary emulsion (water-in-PFC-in-water), and is one in which aqueous droplets are suspended within a PFC droplet and have the following structure: water-in-PFC-in-water (W1/PFC/W2). Double emulsions are utilized because hydrophilic or lipophilic therapeutic agents are not soluble within PFC. Thus, by creating a double emulsion, the droplets are able to carry and deliver both hydrophilic and lipophilic therapeutic agents. In the case of a lipophilic therapeutic agent, the double emulsion would have the following structure: oil-in-PFC-in-water. "Oil" denotes a phase that can solubilize the lipophilic therapeutic agent.

Emulsion Features

As discussed hereinabove, PFC emulsions, with or without a therapeutic payload, can be vaporized into gas bubbles using ultrasound to effect ADV. The delivery of therapeutic agents within a hydrogel scaffold can thus be modulated by adding an ultrasound-triggerable agent, such as a PFC emulsion, to the scaffold. Upon exposure to ultrasound, the PFC phase within the droplets is vaporized, a process termed acoustic droplet vaporization (ADV) [Kripfgans et al., Ultrasound Med Biol. 26(7): 1177-89 (2000)]. Additionally, the therapeutic agent, which was initially sequestered within the droplets prior to ADV, is subsequently released into the scaffold and/or surrounding area. Since ultrasound can be focused non-invasively and at a precise depth with sub-millimeter precision, the location at which ADV occurs can be controlled externally. Thus, gel porosity and release of therapeutic agents in implanted tissue scaffolds are modulated using ADV. Additionally, due to the high oxygen-dissolving ability of liquid PFC [Riess, Chemical Reviews.

101(9):2797-919 (2001)], the droplets, in the absence of ADV, could be used to increase the survival of cells that are located deep within the gel [Chin et al., Biotechnology Progress. 24(2):358-66 (2008)].

In further embodiments, it is contemplated that a device comprises more than one population of PFC droplets. In these embodiments, a first population of PFC droplets would have the property of vaporizing at a first ultrasound frequency and/or acoustic pressure threshold, and a second population of PFC droplets would have the property of vaporizing at a second ultrasound frequency and/or acoustic pressure threshold. Additional embodiments of the disclosure contemplate further populations of PFC droplets, wherein each of the further populations has the property of vaporizing at a unique ultrasound frequency and/or acoustic pressure threshold. The disclosure contemplates that ultrasound frequencies between about 0.5 MHz and about 50 MHz are useful in the devices and methods disclosed herein. Thus, in various embodiments, the disclosure contemplates a tissue scaffold that comprises at least 1, 2, 3, 4, 5, 6, 7, 8, 9, 10, 15, 20 or more populations of PFC droplets. In further embodiments, more than one device, each device comprising a tissue scaffold that comprises one or more populations of PFC droplets, is administered.

The disclosure also provides a device wherein a single population of PFC droplets comprises one or more subpopulations of PFC droplets, wherein each subpopulation has the property of vaporizing at a distinct ultrasound frequency and/or acoustic pressure threshold. Accordingly, in one aspect the disclosure provides a device comprising (a) a tissue scaffold; and (b) an emulsion comprising a population of perfluorocarbon (PFC) droplets comprising a therapeutic agent in the interior thereof, said population of PFC droplets comprising a first subpopulation of PFC droplets with a first mean droplet diameter and a second subpopulation of PFC droplets with a second mean droplet diameter; said first subpopulation of PFC droplets having the property of vaporizing at a first ultrasound frequency and/or acoustic pressure threshold, and said second subpopulation of PFC droplets having the property of vaporizing at a second ultrasound frequency and/or acoustic pressure threshold. In one embodiment, said first ultrasound frequency and/or acoustic pressure threshold and said second ultrasound frequency and/or acoustic pressure threshold are different. In another embodiment, said first ultrasound frequency and/or acoustic pressure threshold and said second ultrasound frequency and/or acoustic pressure threshold are the same.

Further, the disclosure also contemplates that, in some embodiments, each population or subpopulation of PFC droplets, which have the property of vaporizing at a unique ultrasound frequency and/or acoustic pressure threshold, comprises a different therapeutic agent that is released at the same time or at different times. In further embodiments, the populations of PFC droplets each comprise the same therapeutic agent, but may be in different amounts or dosages, which again may be released at the same time or at different times. Dosage can also be controlled by vaporizing additional PFC droplets of the same population in aspects wherein the PFC droplets of the same population are located in separate subvolumes of the scaffold. Combinations of the foregoing embodiments are also contemplated, and are within the skill of the ordinary worker to determine. The populations of PFC droplets allow for unique spatial and temporal delivery of therapeutic agents, as well as affording precise control over said delivery. The ability to vaporize a given population of PFC droplets that comprise a first therapeutic agent at a first time and then vaporize a second population of PFC droplets that comprise a second therapeutic agent at a second time allows for therapeutic regimens that are tailored to a given indication.

In one non-limiting example, a tissue scaffold comprises two populations of PFC droplets, each of which vaporizes at a unique ultrasound frequency and/or acoustic pressure. Each population of PFC droplets comprises the same therapeutic agent, but population one comprises a higher dose of the therapeutic agent relative to the second population. Thus, in a patient who requires a tapering of the dose of a therapeutic agent, the first population of PFC droplets is vaporized before the second population of PFC droplets.

Accordingly, the disclosure contemplates populations of PFC droplets in which the number of therapeutic agents used, the amount of (each of) the therapeutic agent(s), the timing of release of the therapeutic agent(s) and the location of the release of the therapeutic agent(s) are each potential levels of control and tunability for use of a device. Additionally, in further embodiments the biological activity of a precursor of a therapeutic agent is controlled by releasing the activation agent of the therapeutic precursor.

Emulsions, in various embodiments, further comprise a surfactant which stabilizes the emulsion. The surfactant stabilizing the primary emulsion (i.e. water-in-PFC) is a triblock copolymer, including but not limited to a perfluoroether and polyethylene glycol. The surfactant stabilizing the secondary emulsion (i.e. water-in-PFC-in-water) is an aqueous soluble surfactant, including but not limited to proteins, lipids, ionic copolymers, and non-ionic copolymers.

PFC Droplet Size

PFC droplet size contributes to the properties of the tissue scaffold. For example, the vaporization threshold is generally dependent on droplet size, where large droplets vaporize more readily than small droplets. Four factors are important with respect to the diameter of the PFC droplets. First, a larger diameter droplet is desired if maximum loading of the therapeutic agent is desired. Second, the droplet must be able to retain the therapeutic agent in the absence of ADV. Third, following ADV, maximum droplet vaporization and release of the therapeutic agent is desired. Fourth, the droplet diameter must be such that relevant pore sizes are created in the scaffold, either before or after ADV, to allow for invasion of fluid and/or cells. Contrary to general knowledge in the art, and unexpectedly, it is disclosed and exemplified herein that larger diameter PFC droplets (about 100 µm and above) performed better with respect to the aforementioned four factors than did smaller (less than about 100 µm) droplets. Nonetheless, the disclosure contemplates that, in some embodiments, PFC droplets less than 100 µm are utilized.

The average diameter of a PFC droplet for use in the devices and methods of the disclosure are contemplated to be between from about 0.1 µm to about 600 µm. In further embodiments, the average diameter of a PFC droplet is from about 20 µm to about 600 µm. The average droplet diameter and droplet size distribution can be determined using various techniques known in the art, such as optical microscopy, Coulter counter, and light scattering. Different droplet diameters can be obtained by varying the surfactant concentration or the amount of shear force applied to generate the primary or secondary emulsions. In various embodiments, the diameter of a PFC droplet is from about 0.1 µm to about 500 µm, or from about 0.1 µm to about 400 µm, or from about 0.1 µm to about 300 µm, or from about 0.1 µm to about 200 µm, or from about 0.1 µm to about 100 µm, or from about 1 µm to about 500 µm, or from about 1 µm to about 400 µm, or from about 1 µm to about 300 µm, or from about 1 µm to about 200 µm, or from about 1 µm to about 100 µm, or from about 10 µm to about 500 µm, or from about 10 µm to about 400 µm, or from about 10 µm to about 300 µm, or from about 10 µm to about 200 µm, or from about 10 µm to about 100 µm, or from about 50 µm to about 500 µm, or from about 50 µm to about 400 µm, or from about 50 µm to about 300 µm, or from about 50 µm to about 200 µm, or from about 50 µm to about 100 µm. In further embodiments, the diameter of a PFC droplet is from about 0.1 µm to about 50 µm, or from about 0.1 µm to about 75 µm, or from 0.1 µm to about 100 µm, or from 0.1 µm to about 200 µm, or from about 0.1 µm to about 300 µm, or from about 20 µm to about 50 µm, or from about 20 µm to about 75 µm, or from 20 µm to about 100 µm, or from 20 µm to about 200 µm, or from about 20 µm to about 300 µm. In yet further embodiments, the diameter of a PFC droplet is from about 0.1 µm and up to about 10 µm, 20 µm, 25 µm, 30 µm, 35 µm, 40 µm, 45 µm, 50 µm, 55 µm or 60 µm. In additional embodiments, the diameter of a PFC droplet is from about 100 µm and up to about 150 µm, 200 µm, 250 µm, 300 µm, 350 µm, 400 µm, 450 µm, 500 µm, 550 µm or 600 µm. In specific embodiments, the diameter of a PFC droplet is about 0.1 µm, 0.2 µm, 0.3 µm, 0.4 µm, 0.5 µm, 0.6 µm, 0.7 µm, 0.8 µm, 0.9 µm, 1 µm, 1.5 µm, 2 µm, 5 µm, 10 µm, 15 µm, 20 µm, 50 µm, 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, about 300 µm, about 310 µm, about 320 µm, about 330 µm, about 340 µm, about 350 µm, about 360 µm, about 370 µm, about 380 µm, about 390 µm, about 400 µm, about 410 µm, about 420 µm, about 430 µm, about 440 µm, about 450 µm, about 460 µm, about 470 µm, about 480 µm, about 490 µm, about 500 µm, about 510 µm, about 520 µm, about 530 µm, about 540 µm, about 550 µm, about 560 µm, about 570 µm, about 580 µm, about 590 µm, about 600 µm or more.

In still further embodiments, the diameter of a PFC droplet is at least 0.1 µm, at least 0.2 µm, at least 0.3 µm, at least 0.4 µm, at least 0.5 µm, at least 0.6 µm, at least 0.7 µm, at least 0.8 µm, at least 0.9 µm, at least 1 µm, at least 1.5 µm, at least 2 µm, at least 5 µm, at least 10 µm, at least 15 µm, at least 20 µm, at least 50 µm, at least 100 µm, at least 110 µm, at least 120 µm, at least 130 µm, at least 140 µm, at least 150 µm, at least 160 µm, at least 170 µm, at least 180 µm, at least 190 µm, at least 200 µm, at least 210 µm, at least 220 µm, at least 230 µm, at least 240 µm, at least 250 µm, at least 260 µm, at least 270 µm, at least 280 µm, at least 290 µm, at least 300 µm, at least 310 µm, at least 320 µm, at least 330 µm, at least 340 µm, at least 350 µm, at least 360 µm, at least 370 µm, at least 380 µm, at least 390 µm, at least 400 µm, at least 410 µm, at least 420 µm, at least 430 µm, at least 440 µm, at least 450 µm, at least 460 µm, at least 470 µm, at least 480 µm, at least 490 µm, at least 500 µm, at least 510 µm, at least 520 µm, at least 530 µm, at least 540 µm, at least 550 µm, at least 560 µm, at least 570 µm, at least 580 µm, at least 590 µm, at least 600 µm or more.

Volume Fraction

Like PFC droplet size, volume fraction also contributes to the properties of the tissue scaffold. As used herein, "volume fraction" refers to the fraction of the tissue scaffold that is taken up by PFC emulsion. By way of example, a tissue scaffold that contains 1 volume PFC emulsion in 100 total volumes is equal to a 1% volume fraction. Volume fraction is quantitated as a volume: volume measure.

It is disclosed herein that as the volume fraction of the tissue scaffold decreases, certain properties of the gel improve. As exemplified herein, the release of therapeutic agent following ADV is increased approximately 5-fold when a 1% volume fraction is used versus a 10% volume fraction. Quantitation of the release of the therapeutic agent is dependent on the therapeutic agent and methods for such quantitation are well known in the art.

It is contemplated, however, that a volume fraction of between about 0.1% to about 20% is used in the devices and methods of the disclosure. In various embodiments, a volume fraction of between about 0.1% to about 10%, or about 0.1% to about 5%, or about 0.5% to about 10%, or about 1% to about 10%, or about 1% to about 5%, or about 1% to about 15%, or about 1% to about 3%, or about 0.5% to about 5%, or about 1% to about 20% is used in the devices and methods of the disclosure. In specific embodiments, a volume fraction of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% or more may be used in the devices and methods of the disclosure.

In further embodiments, a volume fraction of at least 0.1%, at least 0.2%, at least 0.3%, at least 0.4%, at least 0.5%, at least 0.6%, at least 0.7%, at least 0.8%, at least 0.9%, 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20% or more is used in the devices and methods of the disclosure.

Therapeutic Agents

The present disclosure provides devices that comprise therapeutic agents. "Therapeutic agent," "drug" or "active agent" as used herein means any compound useful for therapeutic or diagnostic purposes. The terms as used herein are understood to mean any compound that is administered to a patient for the treatment or diagnosis of a condition.

Therapeutic agents contemplated for use in the devices and methods of the disclosure include hydrophilic and hydrophobic agents. In various embodiments, the therapeutic agent is selected from the group consisting of a polypeptide, a peptide, a polynucleotide, a viral particle, a gas, a contrast agent, a small molecule, a carbohydrate and an aminoglycoside. Therapeutic agents also include, without limitation, metallic salts, oxides and/or ions.

The present disclosure is applicable to any therapeutic agent for which delivery is desired. Non-limiting examples of such active agents as well as hydrophobic drugs are found in U.S. Pat. No. 7,611,728, which is incorporated by reference herein in its entirety.

Polypeptides

As used herein a "polypeptide" refers to a polymer comprised of amino acid residues. In some aspects of the disclosure, a device comprises a polypeptide as described herein. Polypeptides are understood in the art and include without limitation an antibody, an enzyme and a hormone. Polypeptides of the present disclosure may be either naturally occurring or non-naturally occurring.

Naturally occurring polypeptides include without limitation biologically active polypeptides (including antibodies) that exist in nature or can be produced in a form that is found in nature by, for example, chemical synthesis or recombinant expression techniques. Naturally occurring polypeptides also include lipoproteins and post-translationally modified proteins, such as, for example and without limitation, glycosylated proteins.

Antibodies contemplated for use in the methods and compositions of the present disclosure include without limitation antibodies that recognize and associate with a target molecule either in vivo or in vitro.

Non-naturally occurring polypeptides contemplated by the present disclosure include but are not limited to synthetic polypeptides, as well as fragments, analogs and variants of naturally occurring or non-naturally occurring polypeptides as defined herein. Non-naturally occurring polypeptides also include proteins or protein substances that have D-amino acids, modified, derivatized, or non-naturally occurring amino acids in the D- or L-configuration and/or peptidomimetic units as part of their structure. The term "protein" typically refers to large polypeptides. The term "peptide" typically refers to short polypeptides.

Non-naturally occurring polypeptides are prepared, for example, using an automated polypeptide synthesizer or, alternatively, using recombinant expression techniques using a modified polynucleotide which encodes the desired polypeptide.

As used herein a "fragment" of a polypeptide is meant to refer to any portion of a polypeptide or protein smaller than the full-length polypeptide or protein expression product.

As used herein an "analog" refers to any of two or more polypeptides substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it.

As used herein a "variant" refers to a polypeptide, protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, polypeptides are modified by glycosylation, pegylation, and/or polysialylation.

Fusion proteins, including fusion proteins wherein one fusion component is a fragment or a mimetic, are also contemplated. A "mimetic" as used herein means a peptide or protein having a biological activity that is comparable to the protein of which it is a mimetic. By way of example, an endothelial growth factor mimetic is a peptide or protein that has a biological activity comparable to the native endothelial growth factor. The term further includes peptides or proteins that indirectly mimic the activity of a protein of interest, such as by potentiating the effects of the natural ligand of the protein of interest.

As discussed hereinabove, polypeptides include antibodies along with fragments and derivatives thereof, including but not limited to Fab' fragments, F(ab)2 fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABs), bispecific antibodies and multispecific antibodies, and other antibody derivative or fragments known in the art.

Protein therapeutic agents include, without limitation peptides, enzymes, structural proteins, receptors and other cellular or circulating proteins as well as fragments and derivatives thereof, the aberrant expression of which gives rise to one or more disorders. Therapeutic agents also include, as one specific embodiment, chemotherapeutic agents. Therapeutic agents also include, in various embodiments, a radioactive material.

In various aspects, protein therapeutic agents include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, erythropoietin (EPO), thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor $2\alpha$, cytokine-induced neutrophil chemotactic factor $2\beta$, $\beta$ endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor $\alpha 1$, glial cell line-derived neutrophic factor receptor $\alpha 2$, growth related protein, growth related protein $\alpha$, growth related protein $\beta$, growth related protein $\gamma$, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor $\alpha$, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor $\alpha$, platelet derived growth factor receptor $\beta$, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, WNT ligands, and chimeric proteins and biologically or immunologically active fragments thereof. Examples of biologic agents include, but are not limited to, immuno-modulating proteins such as cytokines, monoclonal antibodies against tumor antigens, tumor suppressor genes, and cancer vaccines. Examples of interleukins that may be used in conjunction with the compositions and methods of the present invention include, but are not limited to, interleukin 2 (IL-2), and interleukin 4 (IL-4), interleukin 12 (IL-12). Other immuno-modulating agents other than cytokines include, but are not limited to bacillus Calmette-Guerin, levamisole, and octreotide.

As described by the present disclosure, in some aspects therapeutic agents include small molecules. The term "small molecule," as used herein, refers to a chemical compound, for instance a peptidometic, that may optionally be derivatized, or any other low molecular weight organic compound, either natural or synthetic. Such small molecules may be a therapeutically deliverable substance or may be further derivatized to facilitate delivery. In some embodiments, a small molecule is a vitamin.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

In various embodiments, therapeutic agents described in U.S. Pat. No. 7,667,004 (incorporated by reference herein in its entirety) are contemplated for use in the compositions and methods disclosed herein and include, but are not limited to, alkylating agents, antibiotic agents, antimetabolic agents, hormonal agents, plant-derived agents, and biologic agents.

Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (e.g., carboplastin, cisplatin and platinum (IV) (Pt (IV))).

Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. Additional antibiotic agents are discussed in detail below.

Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, imatinib mesylate (or GLEEVEC®), and gemcitabine.

Examples of hormonal agents include, but are not limited to, synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), camptothecin compounds (e.g., 20(S) camptothecin, topotecan, rubitecan, and irinotecan), taxanes (e.g., paclitaxel and docetaxel).

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin, Pt(IV) and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

The term "antibiotic agent" as used herein means any of a group of chemical substances having the capacity to inhibit the growth of, or to kill bacteria, and other microorganisms, used chiefly in the treatment of infectious diseases or as a prophylactic to prevent infection. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

Polynucleotides

Polynucleotides contemplated by the present disclosure include DNA, RNA, modified forms and combinations thereof as defined herein. Accordingly, in some aspects, the device comprises DNA. In some embodiments, the DNA is double stranded, and in further embodiments the DNA is single stranded. In further aspects, the device comprises RNA, and in still further aspects the device comprises double stranded RNA, and in a specific embodiment, the double stranded RNA is a small interfering RNA (siRNA) or a microRNA (miRNA). The term "RNA" includes duplexes of two separate strands, as well as single stranded structures. Single stranded RNA also includes RNA with secondary structure. In one aspect, RNA having a hairpin loop is contemplated.

When a device comprises a plurality of polynucleotides, the polynucleotide is, in some aspects, comprised of a sequence that is sufficiently complementary to a target sequence of a polynucleotide such that hybridization of the polynucleotide that is part of the device and the target polynucleotide takes place. The polynucleotide in various aspects is single stranded or double stranded, as long as the double stranded molecule also includes a single strand sequence that hybridizes to a single strand sequence of the target polynucleotide.

A "polynucleotide" is understood in the art to comprise individually polymerized nucleotide subunits. The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases adenine (A), guanine (G), cytosine (C), thymine (T) and uracil (U). Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleotides include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b] [1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

Modified nucleic acids also include peptide nucleic acids (PNAs) as well as locked nucleic acids (LNAs), each of which is known in the art.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

A polynucleotide of the disclosure, or a modified form thereof, is generally from about 5 nucleotides to about 100 nucleotides in length. More specifically, devices comprise polynucleotides that are about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

Plasmids and viral particles, which may comprise expressible coding regions for a protein of interest, are also contemplated by the disclosure. Thus, nucleic acids greater than 100 nucleotides are contemplated. In some embodiments, nucleic acids that are 200, 500, 1000, 2000, 3000, 4000, 5000, 10,000 or more nucleotides in length are contemplated. A protein of interest is any polypeptide that is useful as a therapeutic for a disease condition. A viral particle may comprise a polynucleotide and/or a polypeptide and/or a lipid. A toxin (e.g., a neurotoxin, hemotoxin, cytotoxin and/or necrotoxin), which may in some embodiments comprise a polypeptide, are contemplated for use as a therapeutic agent.

Polynucleotides, as defined herein, also includes aptamers. The production and use of aptamers is known to those of ordinary skill in the art. In general, aptamers are nucleic acid or peptide binding species capable of tightly binding to and discreetly distinguishing target ligands [Yan et al., RNA Biol. 6(3) 316-320 (2009), incorporated by reference herein in its entirety]. Aptamers, in some embodiments, may be obtained by a technique called the systematic evolution of ligands by exponential enrichment (SELEX) process [Tuerk et al., Science 249:505-10 (1990), U.S. Pat. Nos. 5,270,163, and 5,637,459, each of which is incorporated herein by reference in their entirety]. General discussions of nucleic acid aptamers are found in, for example and without limitation, Nucleic Acid and Peptide Aptamers: Methods and Protocols (Edited by Mayer, Humana Press, 2009) and Crawford et al., Briefings in Functional Genomics and Proteomics 2(1): 72-79 (2003). Additional discussion of aptamers, including but not limited to selection of RNA aptamers, selection of DNA aptamers, selection of aptamers capable of covalently linking to a target protein, use of modified aptamer libraries, and the use of aptamers as a diagnostic agent and a therapeutic agent is provided in Kopylov et al., Molecular Biology 34(6): 940-954 (2000) translated from Molekulyarnaya Biologiya, Vol. 34, No. 6, 2000, pp. 1097-1113, which is incorporated herein by reference in its entirety. In various aspects, an aptamer is between 10-100 nucleotides in length.

Carbohydrates and Aminoglycosides

Carbohydrates contemplated for use according to the disclosure include heparin (high molecular weight and low molecular weight), monosaccharides (e.g., glucose, glucosamine, sialic acid), disaccharides (e.g., maltose, trehalose), and polysaccharides (e.g., starch, glycogen, cellulose, chitin).

Aminoglycosides contemplated by the disclosure include, without limitation, antibiotics (e.g., amikacin, arbekacin, gentamicin, kanamycin, neomycin, netilmicin, paromomycin, rhodostreptomycin, streptomycin, tobramycin, and apramycin).

Gases

The disclosure also provides embodiments wherein the device comprises a gas. In a specific embodiment, the device comprises oxygen. In another embodiment, the device comprises nitric oxide (NO).

Methods of increasing the viability of a cell are provided by the disclosure, comprising the step of administering a tissue scaffold to a patient in need thereof, wherein the scaffold comprises PFC droplets comprising oxygen in the interior thereof. In some embodiments, a host cell, which is able to migrate to the interior of the scaffold, finds itself in an environment of relative hypoxia. Release of oxygen by exposing the PFC droplets comprising oxygen to ultrasound relieves the hypoxic environment and increases the viability of the cell.

Contrast Agents/Detectable Markers

In some embodiments, the devices of the present disclosure comprise a contrast agent. The contrast agent, in various embodiments, is selected from the group consisting of gadolinium, xenon, iron oxide, a manganese chelate (Mn-DPDP) and copper. Thus, in some embodiments the contrast agent is a paramagnetic compound, and in some aspects, the paramagnetic compound is gadolinium.

In further embodiments, a device of the disclosure comprises a detectable marker or label. It will be understood that a label contemplated by the disclosure includes any of the fluorophores described herein as well as other detectable labels known in the art. For example, labels also include, but are not limited to, chemiluminescent molecules, radioactive labels, dyes, fluorescent molecules, phosphorescent molecules, and contrast agents as described above.

Suitable fluorescent molecules are well known in the art and include without limitation 1,8-ANS (1-Anilinonaphthalene-8-sulfonic acid), 1-Anilinonaphthalene-8-sulfonic acid (1,8-ANS), 5-(and-6)-Carboxy-2', 7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO-PRO-1-DNA, BO-PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, high Ca, Fura-2, no Ca, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Nissl stain-RNA, Nile Blue, EtOH, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PicoGreen dsDNA quantitation reagent, PO-PRO-1, PO-PRO-1-DNA, PO-PRO-3, PO-PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodaminen Green pH 7.0, Rhodol Green antibody conjugate pH 8.0, Sapphire, SBFI-Na+, Sodium Green Na+, Sulforhodamine 101, EtOH, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO-PRO-1-DNA, YO-PRO-3-DNA, YOYO-1-DNA, and YOYO-3-DNA.

It will also be understood that the detectable markers and/or labels disclosed herein may be used alone, or they may be attached to a therapeutic agent of the disclosure. Methods of attaching a marker or label to a therapeutic agent as disclosed herein are known in the art.

It is also contemplated by the disclosure that, in some aspects, fluorescent polypeptides are used. Any detectable polypeptide known in the art is useful in the methods of the disclosure, and in some aspects is a fluorescent protein including, but not limited to, green fluorescent protein.

Methods

In some aspects, the disclosure provides a method of delivering an effective amount of a therapeutic agent to an individual in need thereof comprising administering a device as disclosed herein to the individual. In some embodiments, the device is for use in regenerative therapies such as therapeutic angiogenesis and bone reconstruction.

The methods of the disclosure generally comprise the steps of preparing a tissue scaffold, delivering the tissue scaffold to one or more sites of interest and exposing the tissue scaffold to ultrasound.

In general, the disclosure provides a device comprising a tissue scaffold and a PFC emulsion. The tissue scaffold, in some embodiments, comprises one or more proteins that, when mixed, polymerize to form the scaffold. As an alternative, a commercially available hydrogel scaffold may be used in the methods provided herein. In a specific embodiment, a tissue scaffold is produced using fibrinogen and thrombin, which are separately reconstituted from a powder. Thus, in some embodiments the tissue scaffold is produced by mixing fibrinogen and thrombin to achieve a given protein density within the scaffold. The reconstituted proteins are then mixed with PFC droplets, which are produced according to published protocols (see, e.g., [Fabiilli et al., Pharm Res. 27(12): 2753-2765 (2010)]) and as described herein, though the protocols described herein contain the following modifications relative to the aforementioned published protocol. First, two different fluorosurfactants were used. Second, albumin and heparin were included in the W2 phase, and third, the secondary emulsion was stirred rather than sonicated. The PFC droplets comprise one or more therapeutic agent(s).

By way of example, a mixture comprising an in situ-polymerizable, biodegradable hydrogel scaffold, such as fibrin, and a PFC emulsion is injected at the site of damaged or diseased tissue. Additional routes of administration are contemplated, and are described herein below. Administration of a device is contemplated to occur 1, 2, 3, 4, 5, 6, 7, 8, 9, 10 or more times each, at one or more sites of an individual. Thus, repeat administration of the device is contemplated. Administration of more than one device is also contemplated, and the multiple devices can each comprise one or more therapeutic agents. Dosing and administration is discussed further below.

The hydrogel scaffold polymerizes within minutes and serves to localize the acoustically-sensitive emulsion at the implantation site. It is also contemplated that the scaffold is allowed to polymerize ex vivo and is subsequently implanted at a site of interest. As discussed hereinabove, the rate of polymerization of the scaffold can be controlled.

Ultrasound is then applied transcutaneously (i.e., non-invasively) to actively control vaporization of the emulsion within the implant to 1) release therapeutic agent(s) encapsulated within the PFC emulsion and 2) modulate the scaffold porosity and/or stiffness/viscoelasticity to enhance cellular in-growth within the device. Controlled release of therapeutic agent(s) from the vaporized droplets, in some embodiments, elicits a regenerative response from host cells (e.g., migration, proliferation, and/or differentiation), and increases in scaffold porosity and/or pore size and/or scaffold stiffness/viscoelasticity enhances invasion of the hydrogel scaffold by these host cells. In one embodiment, the ultrasound is applied to the device a single time, and at a single frequency. In further embodiments, the ultrasound is applied 2, 3, 4, 5, 6, 7, 8, 9, 10 or more times, at one or more frequencies.

In additional embodiments, diagnostic ultrasound is used to provide real-time feedback of changes in porosity. ADV-induced changes in scaffold structure may also accelerate degradation and/or increase the mechanical properties (i.e., stiffness) of the hydrogel scaffold. ADV facilitates scaffold degradation by promoting cellular in-growth into the scaffold, and can change the form factor (i.e., the shape and/or dimensions) of the scaffold post-implantation.

A compelling feature of the method disclosed herein to control release of a therapeutic agent is that ADV can be restricted to subvolumes of the implant by applying the ultrasound with a focused transducer, thus affording tight and active control over the spatial distribution and timing of release of the therapeutic agent(s). The encapsulated agent(s) are released only when and where vaporization of the emulsion occurs. Likewise, structural modifications of the hydrogel scaffold are restricted to subvolumes of the implant exposed to ultrasound.

Additional methods provided by the disclosure include methods of inhibiting expression of a gene product expressed from a target polynucleotide comprising contacting the target polynucleotide with a device as described herein, wherein the contacting is sufficient to inhibit expression of the gene product. Inhibition of the gene product results from the hybridization of a target polynucleotide with a device of the disclosure.

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a device comprising a therapeutic agent such as, without limitation, a polynucleotide. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in vitro in a cell culture assay, generally as a predictable measure of a degree of inhibition that can be expected in vivo resulting from use of a device as described herein.

Dosing and Administration

It will be appreciated that any of the devices described herein may be administered to a mammal in a therapeutically effective amount to achieve a desired therapeutic or diagnostic effect.

The term "therapeutically effective amount", as used herein, refers to an amount of a composition sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by an assay known in the art. The precise effective amount for a subject will depend upon the subject's body weight, size, and health; and the nature and extent of the condition. Therapeutically effective amounts for a given situation can be determined by routine experimentation that is within the skill and judgment of the clinician.

The device can be administered by any route that permits treatment of, for example and without limitation, a disease, disorder or infection as described herein. Additionally, the device, which may comprise a therapeutic agent, may be delivered to a patient using any standard route of administration, including parenterally, such as intra-articularly, intraperitoneally, intrapulmonary, subcutaneously or intramuscularly, intrathecally, topically, as an aerosol, rectally, nasally or by inhalation. Additionally, a device as disclosed herein may be implanted at a site of interest, which can in various embodiments be a site of tissue injury or disease.

Administration may take the form of single dose administration, or the device of the embodiments can be administered over a period of time in divided doses. Also contemplated is the administration of more than one device, either concurrently or separately over a period of time, wherein each device comprises one or more populations of PFC droplets. However the device of the embodiments are administered to the subject, the amounts of device administered and the route of administration chosen should be selected to permit efficacious treatment of the disease condition. Administration of combinations of therapeutic agents (i.e., combination therapy) is also contemplated, provided at least one of the therapeutic agents is in a device as described herein.

Target Site Identification and Composition Delivery

Provided herein are methods of delivering a contrast agent to an individual comprising administering to the individual a device of the disclosure under conditions sufficient to deliver the contrast agent to the individual. Following delivery of the device, in some aspects the method further comprises the step of detecting the contrast agent. Detecting the contrast agent is performed by any of the methods known in the art, including those described herein.

In a specific embodiment, the contrast agent is detected using an imaging procedure, and in various aspects, the imaging procedure is selected from the group consisting of MRI, CT, and fluorescence.

Kits

Also provided are kits comprising a device of the disclosure. In one embodiment, the kit comprises at least one container, the container holding at least one type of device as described herein comprising one or more therapeutic agents as described herein. The container optionally includes one or more additional type of devices comprising one or more additional therapeutic agents.

In another embodiment, the kit comprises at least two containers. The first container holds a protein used to formulate the tissue scaffold. The second container holds one or more proteins that interact with the protein in the first container to trigger polymerization of the tissue scaffold. In further embodiments, the kit comprises a third container comprising an emulsion as described herein.

In each embodiment, the kit optionally includes instructions, each container contains a label, the kit itself includes a label, and the kit optionally includes one or more devices for use as controls.

EXAMPLES

Example 1

Formulation of PFC Emulsion/Hydrogel Scaffold

Basic fibroblast growth factor (bFGF) was reconstituted in phosphate buffered saline (PBS) containing 1% (w/v) bovine serum albumin (BSA) and 10 µg/mL heparin. The bFGF solution was combined with perfluoropentane ($C_5F_{12}$) that contains 8 mg/mL Krytox 157 FSL and 16 mg/mL Krytox 157 FSL-polyethylene glycol copolymer. The mixture was emulsified on ice via sonication. The resulting emulsion, termed a primary emulsion, had the following structure: water-in-PFC. The primary emulsion was then added dropwise into a 10 mg/mL solution of Poloxamer 188 dissolved in PBS containing 1% (w/v) BSA and 10 µg/mL heparin. The mixture was stirred for 10 minutes while on ice. The resulting emulsion, termed a double (or secondary) emulsion, had the following structure: water-in-PFC-in-water. The function of each emulsion component is listed in Table 1.

TABLE 1

Composition of PFC double emulsion

| Component | Function |
| --- | --- |
| bFGF | Growth factor |
| PBS | Aqueous solvent |
| BSA | Stabilizing agent for bFGF |
| Heparin | Stabilizing agent for bFGF |
| Perfluoropentane | PFC liquid that vaporizes into a gas during ADV |
| Krytox 157 FSL | Fluorophilic polymer that stabilizes the primary emulsion |
| Krytox 157 FSL-polyethylene glycol copolymer | Fluorophilic copolymer that stabilizes the primary emulsion |
| Poloxamer 188 | Hydrophilic copolymer that stabilizes the double emulsion |

To generate the hydrogel scaffold, fibrinogen from bovine plasma was dissolved in Dulbecco's Modified Eagle Medium (DMEM). Aprotinin was added to the fibrinogen solution at a concentration of 0.1 U/mL. The fibrinogen solution was combined with thrombin and the double emulsion to form the device.

Example 2

Optimization of PFC Emulsion/Hydrogel Scaffold

Krytox 157 FSL/Krytox 157 FSL Polyethylene Glycol Copolymer

It was experimentally determined that the addition of both polymers, rather than each polymer individually, yielded the most stable primary emulsion and thus the most stable double emulsion. Initially, the concentration of each polymer was 32 mg/mL. However, results obtained for bFGF release using ELISA indicated the potential of polymer-bFGF binding. Thus, the concentrations of polymers for the primary emulsion were decreased. It was determined experimentally that these concentrations yielded the best recovery of bFGF as assayed by ELISA.

Droplet Size

Figure 2:
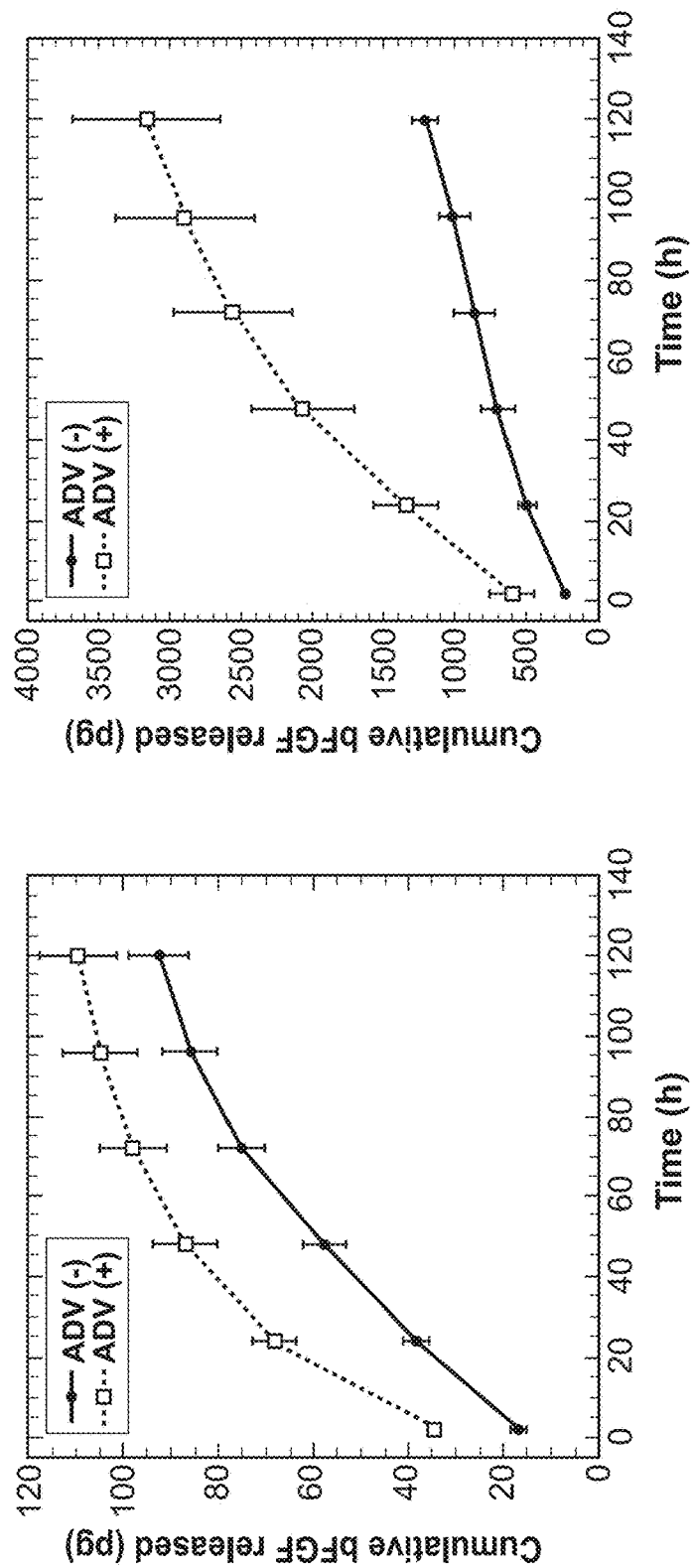
FIG. 2 depicts the in vitro release profiles of bFGF, encapsulated within a PFC double emulsion, and added to a 5 mg/mL fibrin gel. Exposing the gel to 3.5 MHz ultrasound at 0 h caused ADV to occur, thus releasing the encapsulated bFGF. Left: 0.1% (v/v) formulation A (see FIG. 1); Right: 10% (v/v) formulation B (see FIG. 1).

Studies were conducted to determine the optimum droplet size that enabled 1) maximum bFGF loading within the emulsion, 2) stable retention of bFGF in the absence of ADV, 3) maximum droplet vaporization and thus release of bFGF following ADV, and 4) relevant pore sizes required for cellular in-growth into the fibrin matrix. FIG. 1 displays the size distributions of two different emulsion formulations that were evaluated. Formulation B yielded the best results in terms of the four aforementioned criteria. FIG. 2 displays example release profiles for Formulations A and B. Note the larger difference between the ADV(−) and ADV(+) groups in FIG. 2 (right) versus FIG. 2 (left).

Volume Fraction of Emulsion

Figure 3:
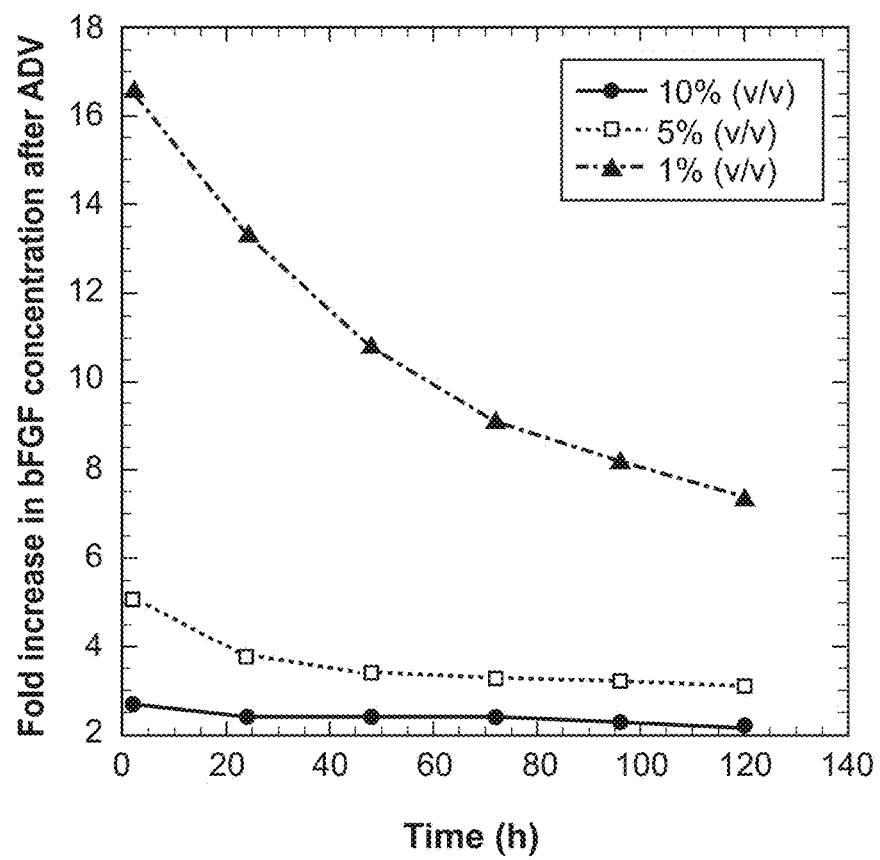
FIG. 3 shows the in vitro release profiles of bFGF, encapsulated within a PFC double emulsion (Formulation B—see FIG. 1) from 5 mg/mL fibrin gels. The volume fraction of the emulsion was varied from 1-10% (v/v).
Figure 4:
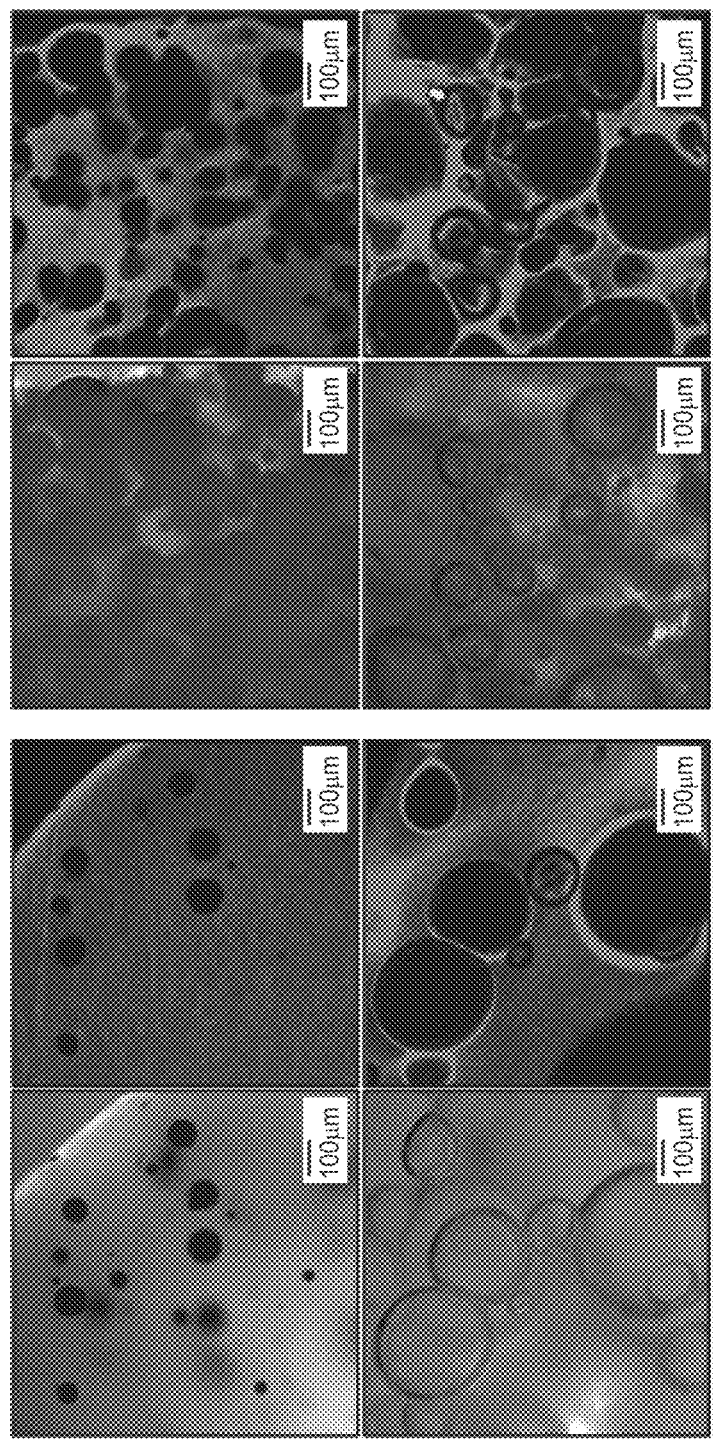
FIG. 4 shows confocal microscopy images of 5 mg/mL fibrin gels containing A) 1% (v/v) Formulation B (see FIG. 1) or B) 10% (v/v) Formulation B. The gels contained Alexa Fluor 647 labeled fibrinogen. The top images of each set correspond to gels that had not been exposed to ultrasound (i.e., no ADV). The bottom images correspond to gels that had been exposed to ultrasound (i.e., ADV). The left and right images in each set are visible and fluorescent images, respectively.

The volume fraction of emulsion in the fibrin gel was varied to determine the optimum fraction required to 1) maximize the differential release of bFGF in the presence and absence of ADV and 2) generate an interconnected pore network necessary for cellular in-growth into the device. FIG. 3 displays the ratio of the bFGF concentration measured in the presence of ADV to that measured in the absence of ADV. By reducing the volume fraction of droplets from 10% to 1%, the differential release increased. Without wishing to be bound by theory, acoustic shadowing is one possible hypothesis for this observed phenomenon. In FIG. 4, example microscopy images reveal that with a 10%

(v/v) volume fraction, an interconnected pore network within the device is obtained following ADV (see arrow in panel B, lower right image).

Gel Dimensions

A gel thickness (i.e., shortest axis) of 0.25-0.4 centimeters (cm) yielded the most homogenous ADV within the gel, as observed visually. If the gel was thicker than 0.5 cm, then ADV was only generated on the outermost surface of the gel. These results were obtained using a single-element, 3.5 MHz transducer (0.75 inch diameter, 1.5 inch focal length).

With a very thick gel, acoustic shadowing caused by bubbles generated by ADV can be a problem. This means that bubbles generated by ADV can block more ADV from occurring depending on the location of the ultrasound focus and the pre-existing bubbles. Therefore, in some embodiments, it is contemplated that one would generate ADV and pores on the surface of the scaffold. The cells would then be allowed to grow into the pores, followed again by ADV after the cellular in-growth. By waiting for cellular in-growth, limitations of acoustic shadowing are overcome since the bubbles will have dissolved during/after cellular in-growth.

Example 3

The experiments described in the following example [and also described in Fabiilli et al. Acta Biomater 9(7): 7399-7409 (2013), incorporated by reference in its entirety] focus on characterizing several formulations of the composites before and after ADV in terms of 1) morphological and mechanical properties; 2) the release of a bioactive therapeutic agent (basic fibroblast growth factor (bFGF)) contained within the $W_1$ phase; 3) enzymatic and cell-based fibrinolysis of the scaffold; and 4) viability of cells co-encapsulated in the composite scaffold.

Preparation and Characterization of Emulsion

The double emulsion was prepared by modifying a previously published method [Fabiilli et al., Pharm Res 27: 2753-65 (2010)]. The primary emulsion ($W_1$/PFC) was formed by dissolving Krytox 157 FSL (CAS#51798-33-5, DuPont, Wilmington, Del., USA), a perfluoroether with carboxylic acid functionality, and Krytox 157 FSL-polyethylene glycol copolymer in PFP (CAS#678-26-2, Strem Chemicals, Inc., Newburyport, Mass., USA) at concentrations of 0.5% (w/w) and 1.0% (w/w), respectively. Krytox, including its derivatives and copolymers, has been used to stabilize emulsions in in vitro studies with mammalian cells and *C. elegans* [Clausell-Tormos et al., Chemistry and Biology 15: 427-37 (2008)] as well as in in vivo studies with chicken embryos [Couture et al., Med Phys 38: 1116-23 (2011)] and rats [Couture et al., Med Phys 39: 5229-37 (2012)]. The PFP phase was then combined with an aqueous solution of bFGF, reconstituted at 50 µg/mL in phosphate buffered saline (PBS) containing 1% (w/v) bovine serum albumin (BSA) and 10 µg/mL heparin, at a volumetric ratio of 2.1:1. Heparin was included because it has been shown to protect bFGF from degradation [Sommer et al., J Cell Physiol 138: 215-20 (1989)]. The phases were emulsified, while in an ice bath, using the microtip accessory of a sonicator (model 450, 20 kHz, Branson, Danbury, Conn., USA) operating at 125 W/cm² for 30 seconds in continuous mode. The resulting primary emulsion was added drop-wise at a 1:2 volumetric ratio to a 10 mg/mL solution of Poloxamer 188 (Sigma-Aldrich, St. Louis, Mo., USA), dissolved in PBS containing 1% (w/v) BSA and 10 µg/mL heparin, which was in an ice bath and being stirred at 1100 rpm for 10 minutes. To minimize carryover of non-emulsified bFGF, the double emulsion was washed by allowing the emulsion to settle, removing the supernatant, and adding fresh PBS with 1% BSA and 10 µg/mL heparin. The concentration of bFGF in the supernatant was assessed using an enzyme-linked immunosorbent assay (ELISA) (DY233, R&D Systems, Inc., Minneapolis, Minn., USA). The emulsion was sized using a Coulter counter (Multisizer 3, Beckman Coulter Inc., Brea, Calif., USA). Except for the bFGF release experiments, sham double emulsions were used, which did not contain bFGF in the $W_1$ phase. To assess the double emulsion structure, fluorescein sodium salt (Sigma-Aldrich) was dissolved in the $W_1$ phase. The resulting emulsion was diluted in PBS and mounted on a microscope slide in a coverwell imaging chamber (Electron Microscopy Sciences, Hatfield, Pa.). Confocal fluorescent images of the droplets were taken using an inverted SP5× microscope with a 63× objective (Leica, Wetzlar, Germany). For all experiments, the emulsion was used "as is" without any further purification or size separation.

Results—Characterization of Emulsion

Figure 5:
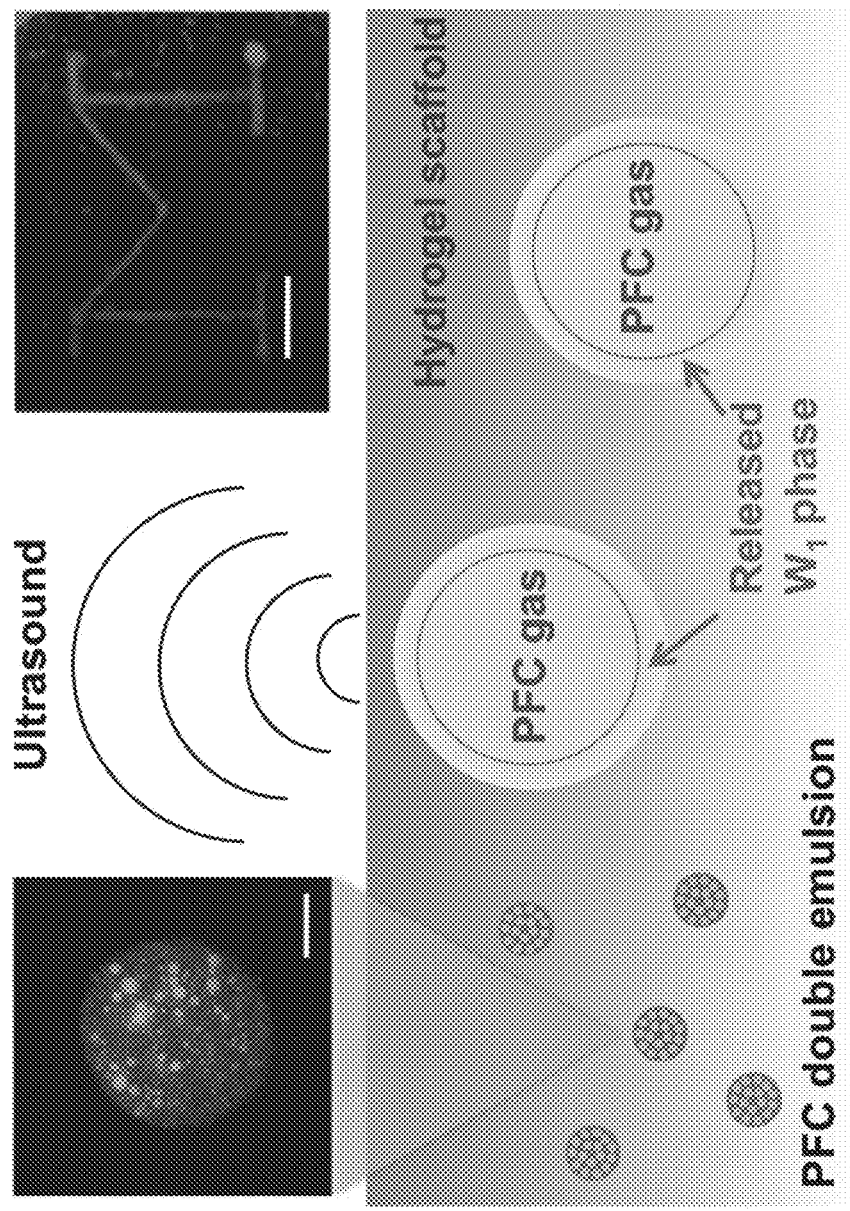
FIG. 5 is a schematic representation of drug release by ADV in a hydrogel scaffold. Bottom: A water-in-PFC-in-water ($W_1$/PFC/$W_2$) double emulsion, containing a growth factor in the $W_1$ phase, is encapsulated within the scaffold. Upon exposure to acoustic amplitudes greater than the ADV threshold of the emulsion, the PFC within the droplets is vaporized, thus releasing the $W_1$ phase. Top left: Confocal fluorescence image of a PFC double emulsion droplet (scale bar=10 µm). Smaller aqueous droplets, containing a water-soluble payload such as fluorescein or bFGF, are enveloped by a larger PFC globule. Top right: Visible image of a 10 mg/mL fibrin gel containing 5% (v/v) double emulsion after targeted exposure to ultrasound. The 'block M' consists of gas bubble generated by ADV. Scale bar=4 mm.
Figure 6:
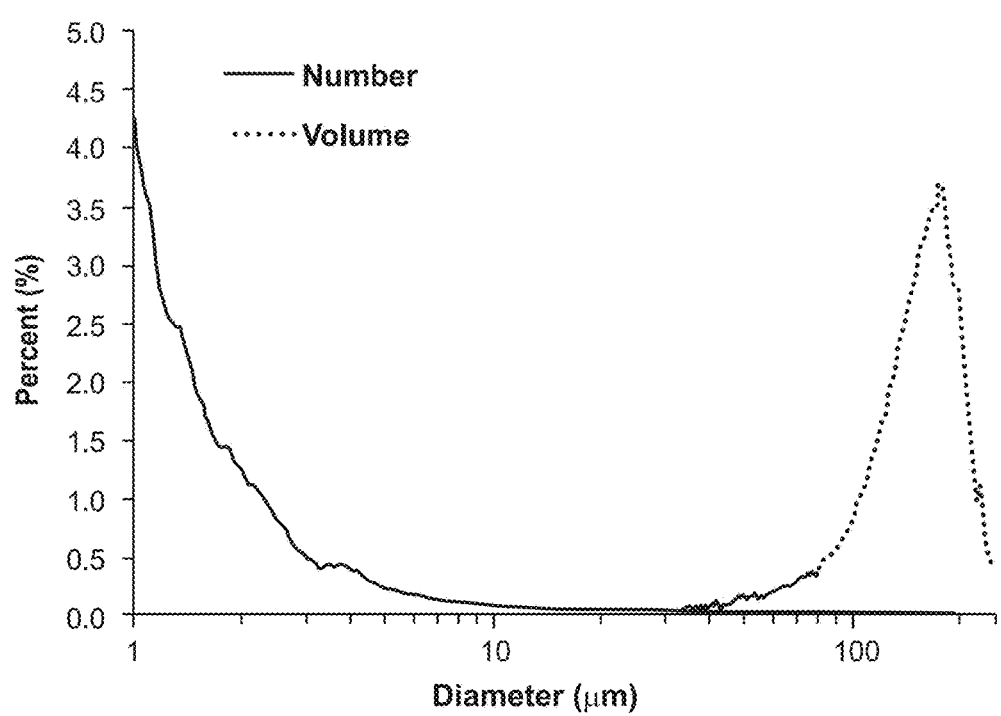
FIG. 6 depicts the number and volume-weighted size distributions of a PFC double emulsion containing bFGF. Droplets were sized using a Coulter counter within 2 hours of preparation.

FIG. 5 displays a micrograph of the double emulsion structure used to encapsulate bFGF. For clarity, a relatively large droplet is shown, though smaller droplets exhibited similar double emulsion structures. The mean outer droplet diameter was 4.1±0.3 µm with 0.7% (by number) and 87.3% (by volume) of the double emulsion droplets greater than 100 µm (FIG. 6). No differences in emulsion structure or particle size were observed when comparing sham emulsions versus emulsions containing bFGF or fluorescein in the $W_1$ phase. Analysis of the supernatant indicated that >99% of bFGF remained encapsulated in the emulsion after washing.

Hydrogel Fabrication

Fibrin gels and droplet-hydrogel composites with either 5 or 10 mg/mL clottable protein were prepared by combining bovine fibrinogen (Sigma-Aldrich) dissolved in Dulbecco's Modified Eagle Medium (DMEM), with bovine thrombin (2 U/mL, Thrombin-JMI, King Pharmaceuticals, Bristol, Tenn., USA), and 0%, 1%, or 5% (v/v) of the double emulsion. All solutions besides the emulsion were degassed under vacuum prior to polymerization. Gels were allowed to polymerize for 30 minutes at room temperature prior to use. For cell culture and bFGF release studies, 0.5 mL gels (final dimensions: 16 mm diameter, 2 mm height) were cast in wells of 24-well culture plates (Fisher Scientific, Pittsburgh, Pa., USA). For mechanical testing, 2.5 mL gels (final dimensions: 36 mm diameter, 2 mm height) were cast in 6-well HT Bioflex plates (Flexcell International Co., Hillsborough, N.C., USA). In some experiments the gels were doped with Alexa Fluor 647 (AF647)-fibrinogen (Invitrogen, Grand Island, N.Y., USA). A summary of the composite hydrogel formulations can be seen in Table 2.

TABLE 2

Composition of droplet-hydrogel scaffolds.
The concentrations of bFGF and PFP are expressed per gel volume.
The thrombin concentration was similar for all formulations (2 U/mL).

Composite Formulation

| Fibrin (mg/mL) | Emulsion (% v/v) | bFGF (ng/mL) | PFP (mg/mL) |
|---|---|---|---|
| 5 | 0 | 0 | 0 |
| 5 | 1 | 51.3 | 3.3 |

TABLE 2-continued

Composition of droplet-hydrogel scaffolds.
The concentrations of bFGF and PFP are expressed per gel volume.
The thrombin concentration was similar for all formulations (2 U/mL).
Composite Formulation

| Fibrin (mg/mL) | Emulsion (% v/v) | bFGF (ng/mL) | PFP (mg/mL) |
|---|---|---|---|
| 5 | 5 | 256.4 | 16.7 |
| 10 | 0 | 0 | 0 |
| 10 | 1 | 51.3 | 3.3 |
| 10 | 5 | 256.4 | 16.7 |

Ultrasound Exposure

A calibrated 3.5 MHz single-element transducer (1.9 cm diameter, 3.81 cm focal length, A381S, Panametrics, Olympus NDT, Waltham, Mass., USA) was used to generate ADV within the gels. Acoustic pulses generated by the transducer—10 cycles, 10 ms pulse repetition period, 12.9 MPa peak compressional pressure (free field), 6.0 MPa peak rarefactional pressure (free field)—were achieved using a master function generator (33120A, Agilent Technologies, Palo Alto, Calif., USA) gated by a secondary function generator (3314A, Agilent Technologies). The driving signal was sent to a power amplifier (60 dB, model 350, Matec Instrument Co., Northborough, Mass., USA) and then directly to the transducer. The general approach to exposing the scaffolds to ultrasound was to fixture the plate in which the hydrogels were cast at the air-water interface of a 37° C. water bath. Acoustic pulses were transmitted through the bottom of the plate into each sample. The transducer was moved to expose the entirety of each gel to ultrasound until vaporization was complete, as assessed visually by cessation of bubble formation; the typical exposure time for complete vaporization was approximately 15 seconds. No temperature increases were observed in the gels using the aforementioned exposure setup and acoustic conditions. Sham controls were placed in the tank for a comparable time but not exposed to ultrasound. To demonstrate spatial patterning of ADV within the composites, the ultrasound transducer was rastered via a computer-controlled positioning system at a speed of 1 mm/s in a pre-defined pattern.

Composite Morphology

Morphological features of droplet-hydrogel composites before and after ADV were characterized macroscopically by photography as well as microscopically using transmitted light and confocal fluorescence. Within 1 hour of ultrasound or sham treatment, gels were rinsed briefly in PBS and mounted on microscope slides in coverwell imaging chambers with a small volume of PBS. Using an inverted SP5× microscope with a 10× objective, gross morphological features of the composites were captured by imaging transmitted light from the 488 nm line of an Argon laser (Leica). Ultrastructural features of the fibrin scaffold were captured by imaging the fluorescence of AF647-tagged fibrinogen that was excited with the 647 nm line of a supercontinuum white light laser (Leica). Fluorescence images were captured at 5 μm intervals through 100 μm thick stacks. ImageJ (ver 1.47b, National Institutes of Health, USA) was used to uniformly adjust the brightness and contrast in images of transmitted light and to construct maximum projections of the stacks of fluorescence images.

Results—Morphology of Droplet-Hydrogel Composites

Figure 7:
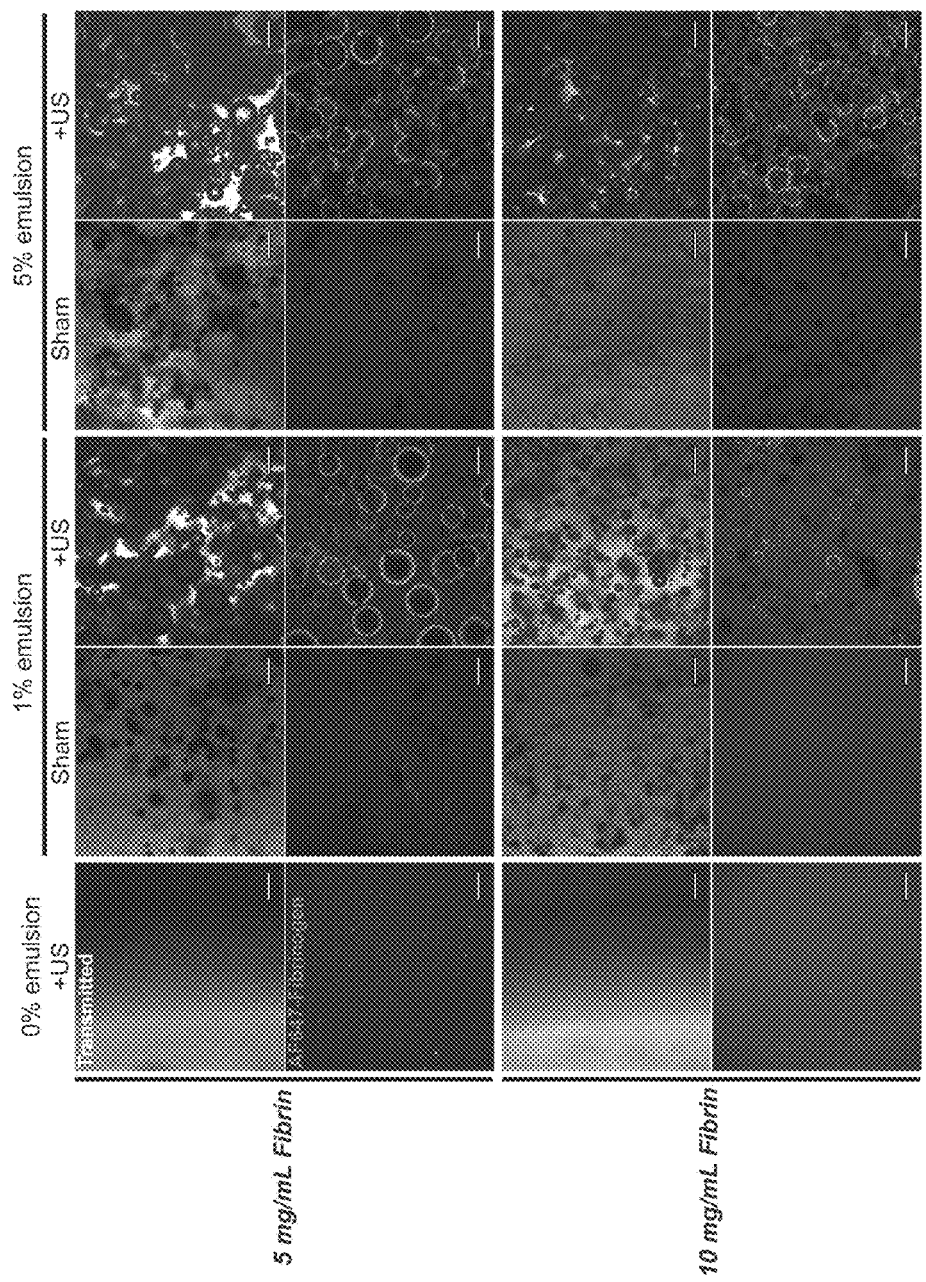
FIG. 7 shows morphologies of droplet-hydrogel composites with and without exposure to ultrasound (US). Representative images of transmitted light (488 nm, rows 1 and 3) and maximum projections from 100 µm stacks of confocal fluorescence images (AF647-fibrinogen, rows 2 and 4) depict ADV-induced changes in scaffold architecture for 5 mg/mL and 10 mg/mL fibrin hydrogels doped with 0%, 1%, or 5% (v/v) double emulsion. Panels at left show the morphology of fibrin hydrogels without droplets that were exposed to ultrasound; sham controls appeared similar. Due to the curved surfaces of the samples, gradients were observed in the intensity of transmitted light for the hydrogels without emulsion. Scale bars=200 µm.

As seen macroscopically in FIG. 5 (inset), bubbles can be spatially patterned within the composite scaffold by rastering a focused ultrasound transducer (−6 dB lateral beam width: 0.8 mm). For a 10 mg/mL gel with 5% (v/v) emulsion, the lateral and axial dimensions of the bubble cloud (i.e., opaque features) were 0.8 mm and 3-4 mm, respectively. For a range of fibrin densities and emulsion volume fractions (Table 2), transmitted light and confocal fluorescence microscopy were used to characterize droplet- and ADV-induced changes in the ultrastructure of fibrin scaffolds (FIG. 7). Control gels lacking droplets exhibited a nearly homogeneous distribution of AF647-fibrinogen and few structures visible by transmitted light; no differences in scaffold morphology were found between ultrasound-exposed and sham controls. Composite gels containing 1% or 5% emulsion exhibited numerous round opacities in the transmitted light images and gaps in the fluorescence, indicating that the fibrin polymerized around the droplets. Exposure of the composite gels to ultrasound induced vaporization of the emulsion and the generation of bubbles/pores ranging in size from tens of microns to millimeters in diameter. Fluorescence images revealed a consolidation of the fibrin at the margins of these bubbles, as indicated by an elevated fluorescence intensity in those regions. Qualitatively, droplets in the 5 mg/mL fibrin scaffolds yielded larger bubbles than in the 10 mg/mL scaffolds, and there were fewer unvaporized droplets following ultrasound exposure in the lower density fibrin. In contrast to the gels with 1% emulsion, gels with 5% emulsion appeared to establish an interconnected network of bubbles/pores. These results show that ADV can be used to introduce bubbles and thereby modify the ultrastructure of droplet-hydrogel composites.

Exposure of acoustic droplet-hydrogel composites to ultrasound readily induced the formation of bubbles in all of the formulations examined. Interestingly, bubble number and size appeared to be inversely related to fibrin density, suggesting that formation and growth of the bubbles can be reduced by increasing the stiffness of the surrounding hydrogel. This observation is consistent with the finding that the acoustic pressure threshold for vaporization of PFC emulsions increases with the viscosity of the surrounding medium [Fabiilli et al., IEEE Trans Ultrason Ferroelectr Freq Control 56: 1006-17 (2009)]. The vaporization threshold is also dependent on droplet size, where large droplets are expected to vaporize more readily than small droplets. Indeed, for both densities of fibrin tested, an unvaporized fraction of droplets was observed following ultrasound exposure that was comprised primarily of smaller (<20 μm diameter) droplets indicating that these droplets were exposed to acoustic pressures that were below their ADV thresholds. Increasing the volume fraction of droplets in the composites increased the number of bubbles formed following exposure to ultrasound but did not appear to otherwise influence ADV. It is contemplated that at higher droplet concentrations acoustic "shadowing" will occur in which ADV-generated bubbles scatter incoming ultrasound energy and block the vaporization of droplets in the far field [Lo et al., Ultrasound Med Biol 32: 95-106 (2006)]. The findings described herein demonstrate that ADV thresholds can be "tuned" through modulation of droplet size and material properties of the surrounding medium.

ADV-generated PFC bubbles may provide a structural template for increasing the pore size of the fibrin scaffold. A wide range of pore sizes within a scaffold can be conducive for a variety of regenerative processes, such as fibroblast ingrowth (5-15 μm) or rapid vascularization (>500 μm)

[Whang et al., Tissue Engineering 5:35-51 (1999)]. In the in vitro studies presented herein, most of the bubbles examined by transmitted and fluorescence microscopy remained filled with gas, although some bubbles (typically at the surfaces of the gels) were filled with fluid indicating that the PFC gas had escaped. Many bubbles were clustered together and exhibited breaches in the fibrin scaffold between adjacent bubbles, indicating that formation of a semi-continuous pore network is possible with ADV. Although retention of PFC may be useful and is contemplated in some embodiments (e.g., delivery of dissolved oxygen within a thick construct [Maillard et al., Biomaterials 32:9282-9 (2011)]), gas-filled bubbles present barriers to cellular invasion and transport of nutrients. Clearance of PFC gas from the composite materials in vivo will depend on initial proximity to a vascular supply and subsequent invasion during angiogenesis. It is contemplated that gas exchange in the bubbles for interstitial fluid will establish a fluid-filled pore network that is more amenable to solute transport and vascular invasion than pre-ADV composites or bubble-filled composites post-ADV.

Rheological Testing

The mechanical properties of droplet-hydrogel composites were measured by dynamic torsion tests. Within approximately 6 hours of sham or ultrasound exposures, samples were cut to 8 mm diameter with a biopsy punch (Miltex, York, Pa., USA) and the thickness was measured in 3 locations using digital calipers (Mitutoyo, Kawasaki, Japan). Each sample was then loaded between platens in an AR-G2 rheometer (TA Instruments, New Castle, Del., USA). The test geometry consisted of an 8 mm diameter upper plate parallel with a temperature-regulated base plate set to 37° C. Both surfaces were fit with adhesive-backed waterproof emery paper (3M, St. Paul, Minn., USA) to minimize slip. Samples were compressed by 10% of the initial thickness and allowed to equilibrate for 5 minutes. The samples were then subjected to oscillatory shear at 0.1 and 1 Hz with a strain amplitude of 1%. Measurements of the complex shear modulus (G*) and dissipation factor (i.e., tangent of the phase angle, δ) reflect the stiffness and viscoelasticity of the materials, respectively.

Results—Mechanical Properties of Droplet-Hydrogel Composites

Figure 8:
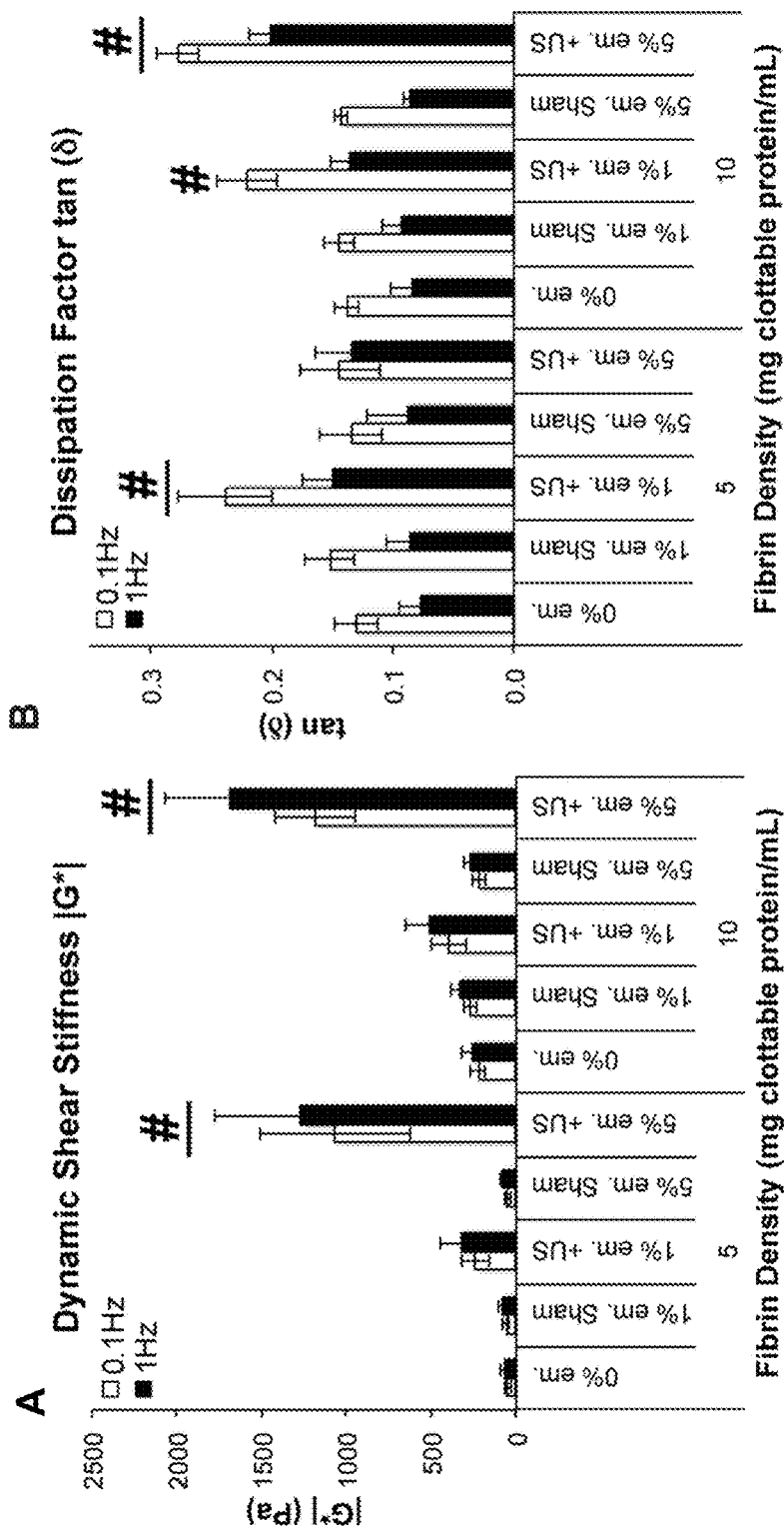
FIG. 8 shows mechanical properties of droplet-hydrogel composites with and without exposure to ultrasound (US). Oscillatory torsional shear tests (1% strain magnitude at 0.1 and 1.0 Hz) were used to measure the complex shear modulus |G*| (A) and dissipation factor tan (δ) (B) of the materials within approximately 6 hours of sham or US treatment. Data are shown as mean±standard deviation for n=5. # p<0.05 vs. sham controls.

Dynamic shear tests demonstrated that ADV caused dramatic increases in the stiffness of acoustic droplet-fibrin composites. The addition of emulsion without exposure to ultrasound did not change the shear properties of the composite for any of the formulations examined. But after exposure to ultrasound and vaporization of the emulsion, the droplet-hydrogel composite scaffolds exhibited substantial and statistically significant increases in the complex shear modulus, |G*|, compared to sham-treated controls (FIG. 8A). In the lower density fibrin gels, vaporization of 1% emulsion increased the shear stiffness by approximately 300% and vaporization of 5% emulsion increased the shear stiffness by 1600-2100%. The higher density fibrin gels exhibited less robust increases in shear properties, with vaporization of 1% emulsion increasing stiffness by approximately 50% and vaporization of 5% emulsion increasing the stiffness by approximately 500% over sham controls. These increases were evident at both 0.1 and 1 Hz test frequencies. The increases in shear stiffness following ADV were also generally accompanied by increases in tan δ, which is an indicator of the viscoelasticity of the material. Higher values of tan δ indicate a more dissipative mechanical response. For 5 mg/mL fibrin with 1% emulsion and 10 mg/mL fibrin with either 1% or 5% emulsion, the ADV-induced increases in tan δ were statistically significant (FIG. 8B). These results show that ADV can be used to modify the mechanical properties of droplet-hydrogel composites.

ADV increased the stiffness of acoustic droplet-hydrogel composites. The results of dynamic torsion tests described herein showed that the complex shear modulus increased several fold, in an emulsion dose-dependent fashion, following exposure to ultrasound for the two densities of fibrin that were examined. A previous study demonstrated that the inclusion of microbubbles within a hydrogel scaffold increased the elastic modulus [Epstein-Barash et al., Biomaterials 31: 5208-17 (2010)]. The increases in stiffness after ADV may be attributed, in part, to the consolidated fibrin at the margins of the bubbles. During ADV, the PFC phase of the droplets undergoes a substantial volume expansion (approximately 150 fold in water) [Kripfgans et al., Ultrasound Med Biol 26: 1177-89 (2000)] that in the composites is partially resisted and partially dissipated by the fibrin scaffold. The pressure in the bubble is sufficient to deform the fibrin such that the network is consolidated in the radial direction (with respect to the bubble) and stretched in the circumferential direction. Fibrin exhibits robust strain-stiffening behavior in which the storage modulus increases up to 40 fold over the range of 10-40% shear strain [Bale et al., Thromb Res 52: 565-72 (1988); Shah et al., Rheol Acta 36: 262-8 (1997)]. It is likely that the local increase in fibrin stiffness associated with the circumferential stretch imparted by the bubbles contributes to the increases in bulk modulus for ultrasound-treated composites. Ultrasound-treated droplet-hydrogel composites also exhibited, in general, higher dissipation factors (tan (δ)) than their respective sham-treated control gels. The sources of the more viscous mechanical responses include, without limitation, drag associated with the gas-liquid interface, bubble rearrangement, and/or added molecular-level relaxations in the fibrin network due to the applied stretch. Collectively, these ADV-induced changes in hydrogel mechanical properties are contemplated to have utility in directing the behavior of cells entrapped within, or migrating into, the composite materials. Previous studies have demonstrated that mesenchymal progenitors are sensitive to both the elastic modulus [Engler et al., Cell 126: 677-89 (2006), incorporated herein by reference in its entirety] and loss (viscous) modulus [Cameron et al., Biomaterials 32: 5979-93 (2011)] of their substrate. In addition, spatially-restricted changes in scaffold mechanics may be induced through targeted application of ultrasound for the generation of graded constructs such as osteochondral interfaces.

In Vitro Release of bFGF

Gels were prepared as described above except that 0.1 U/mL aprotinin from bovine lung (Sigma-Aldrich) was included. The aprotinin was added to inhibit the enzymatic/proteolytic degradation of the fibrin gel. After polymerization, each gel was covered with 1 mL endothelial basal medium (EBM, ENDO-Basal medium, Angio-Proteomie, Boston, Mass., USA) supplemented with 10 μg/mL heparin (Sigma-Aldrich) and 5% fetal bovine serum (FBS, Hyclone, Thermo Scientific, Logan, Utah, USA). Ultrasound and sham treatments were applied to the scaffolds as described above and then moved to a standard tissue culture incubator. Every 24 hours for 6 days, 50% of the medium was collected and replaced with fresh medium. After 5 days, sham controls were exposed to ultrasound to evaluate the potential for delayed release of bFGF. The concentration of bFGF in the releasates was measured by ELISA.

To assess the bioactivity of bFGF released through ADV, a portion of each releasate was applied to monolayer cultures of human umbilical vein endothelial cells (HUVECs, Angio-Proteomie). The cells were initially plated at 1.25× $10^4$ cells/cm$^2$ in a 96-well dish in endothelial growth medium (EGM, ENDO-Growth medium, Angio-Proteomie). After 24 hours, the medium was replaced with EBM supplemented with 5% FBS and the next day the cells were treated with releasates from the droplet-hydrogel composites. Control cultures were treated with 0-5 ng/mL bFGF in EBM with 5% FBS and 10 µg/mL heparin. Every 24 hours the medium was replaced with 100 µL of releasate collected that day (i.e., 10% of the total collected volume). After 5 days the metabolic activity of the cultures was assessed by the alamarBlue assay (Invitrogen) according to the manufacturer's instructions. Briefly, the cells were incubated with 10% (v/v) alamarBlue reagent in EBM for 2.5 hours, and the fluorescence ($\lambda_{ex}$: 550 nm/$\lambda_{em}$: 590 nm) of the supernatants was measured in a Spectramax Gemini plate reader (Molecular Devices, Sunnyvale, Calif., USA).

Results—ADV-Triggered Release of bFGF from Acoustic Droplets

Figure 9:
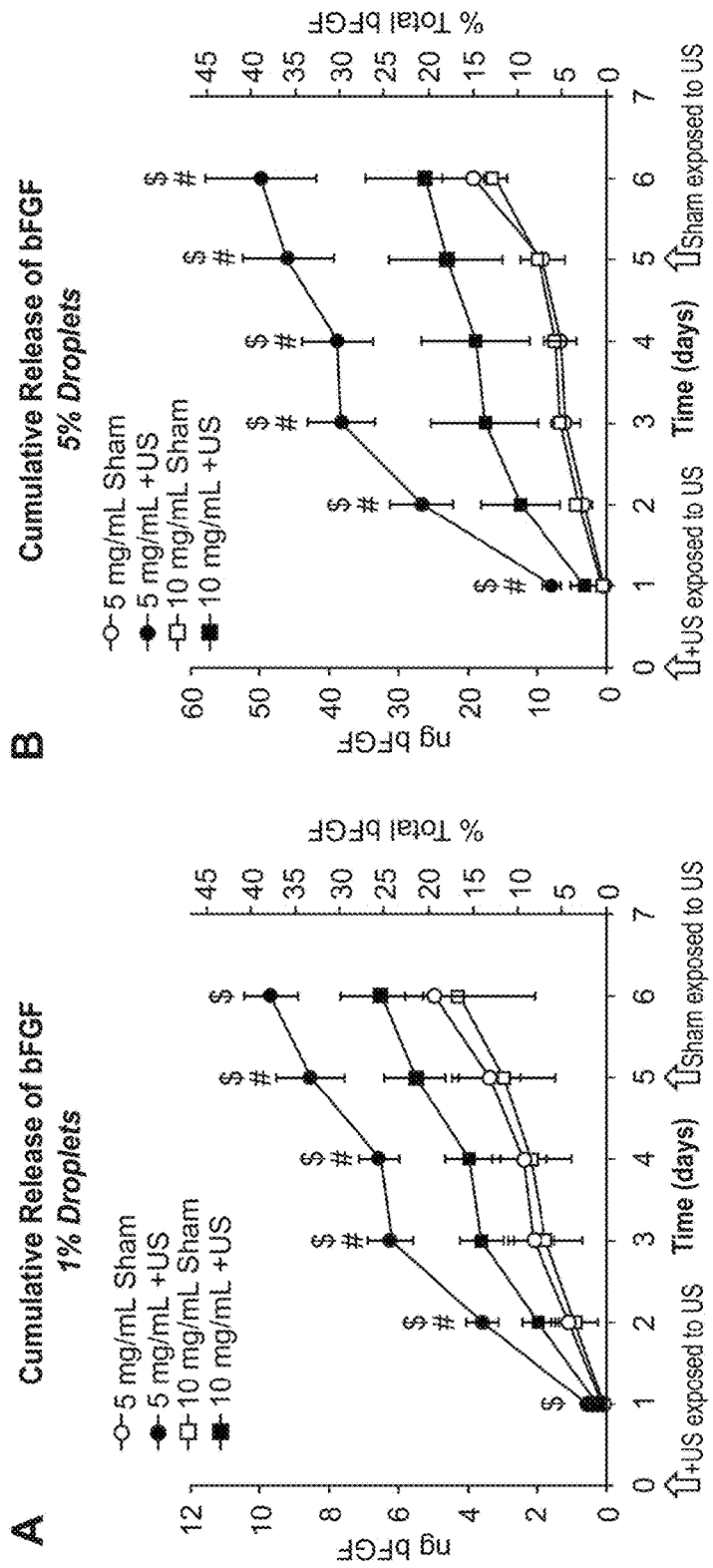
FIG. 9 depicts ADV-induced release of bFGF from droplet-hydrogel composites. +US groups were exposed to ultrasound at the start of the experiment (i.e., time=0 days) and shams were exposed to ultrasound after collection of releasate on day 5. Cumulative release profiles are shown in (A) and (B) for 5 mg/mL and 10 mg/mL fibrin composites. Data are shown as mean±standard deviation for n=5. $ p<0.05 for 5 mg/mL fibrin +US vs. sham control. # p<0.05 for 10 mg/mL fibrin +US vs. sham control. For sham controls with 5% emulsion (for both 5 mg/mL and 10 mg/mL fibrin) treated with ultrasound at day 5, rates of release were found to be significantly higher at day 6 compared to projected values computed using the 95% confidence interval of the slope between days 1-5.

FIG. 9 shows that droplet-hydrogel composites exposed to ultrasound released significantly more bFGF than sham-treated controls, with peaks in release occurring between days 2 and 3. Low levels of release from sham controls were detected throughout the experiment and were independent of fibrin density. After exposure to ultrasound on the fifth day, the day 6 rates of release of sham controls with 5% emulsion were significantly greater than on day 5 indicating that a "delayed release" could be induced by delaying ADV. Ultrasound-treated 5 mg/mL fibrin gels with 5% emulsion released approximately 50 ng of bFGF over 6 days, or about 39% of the total bFGF initially loaded in each gel whereas ultrasound-treated 10 mg/mL fibrin gels with 5% emulsion released about 20% of the initial bFGF. For 5 mg/mL fibrin gels with 1% emulsion, ultrasound treated samples released 2.5-fold more bFGF than sham controls over the first 5 days of the experiment. Five-fold more bFGF was released from ultrasound-treated samples than controls for 5 mg/mL fibrin gels with 5% emulsion. For both doses of emulsion in 10 mg/mL fibrin the ultrasound-induced increases in bFGF were approximately 2-fold higher than the respective sham controls. These data demonstrate that droplet-hydrogel composites can provide controlled release of a growth factor in vitro.

Figure 10:
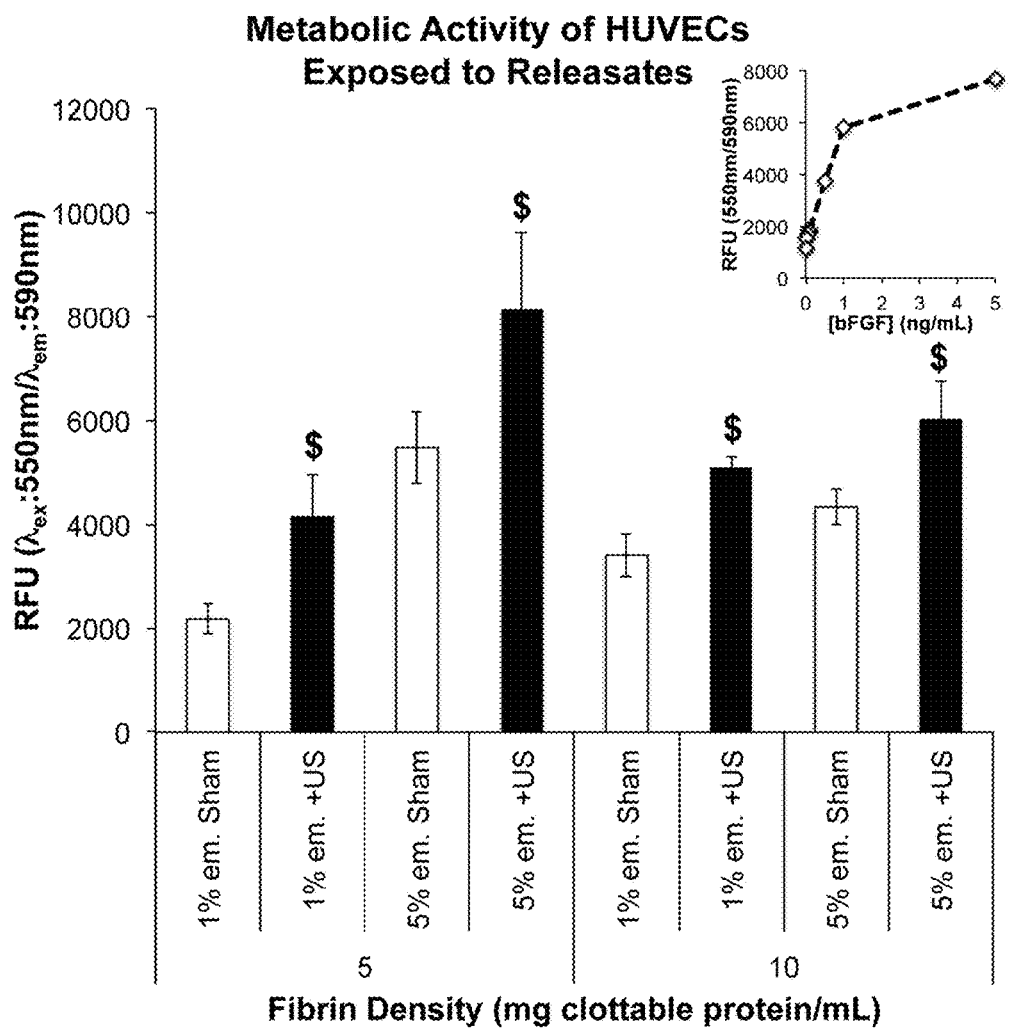
FIG. 10 shows the metabolic activity of HUVECs after 5 days of incubation with releasates from droplet-hydrogel composites. Cells were incubated with releasates collected that day. Data are shown as mean±standard deviation for n=5. $ p<0.05 vs. sham control. Inset shows activity of HUVECs treated with known concentrations of bFGF.

The bioactivity of bFGF released by ADV in droplet-hydrogel composites was evaluated by culturing HUVECs with the releasates from the release study. This approach was based on the premise that bioactive bFGF would increase the metabolic activity of the cell cultures by promoting survival and/or stimulating proliferation. After 5 days of treatment, HUVECs treated with releasates from ultrasound-exposed droplet-hydrogel composites were found to have exhibited significantly higher metabolic activities than their respective sham controls for 5 mg/mL fibrin with 1% (92% increase) or 5% emulsion (48% increase) and 10 mg/mL fibrin with 1% (49% increase) or 5% droplets (39% increase) (FIG. 10). These results show that bFGF released by ADV is functional and bioactive.

Ultrasound caused significant increases in the amount of bFGF released from the growth factor-loaded composite scaffolds. A larger differential release (i.e., sham versus+US) was observed from the 5 mg/mL gels than the 10 mg/mL gels, which is consistent with the observation that more unvaporized emulsion remained in the higher fibrin density gels after ultrasound exposure. For the release study, the ultrasound propagation path was through the bottom of a polystyrene well dish, which has an acoustic attenuation of approximately 4.5 dB/cm/MHz [Garvin et al., Ultrasound Med Biol 36: 1919-32 (2010)]. The use of a more acoustically-transparent exposure window (ex. approximately 0.7 dB/cm/MHz for a silastic-bottomed BioFlex plate [Garvin et al., Ultrasound Med Biol 36: 1919-32 (2010)]) could minimize the amount of unvaporized emulsion. By comparison, the attenuation coefficient of the 10 mg/mL fibrin scaffolds with 0% emulsion was determined to be in the range of 0.04-0.14 dB/cm/MHz, which is lower than the attenuation of soft tissue (0.2-0.5 dB/cm/MHz) [Wells et al., J R Soc Interface 8:1521-49 (2011)].

Without wishing to be bound by theory, the release of bFGF in the absence of ultrasound is attributed to two potential mechanisms: 1) the diffusion of bFGF from the $W_1$ phase into the surrounding gel medium in the absence of droplet vaporization and 2) spontaneous vaporization of the PFC phase of the emulsion. Some spontaneous vaporization of the emulsion was observed in sham gels during the 6-day incubation period, suggesting that the boiling point elevation experienced by PFP double emulsion is different than that experienced by single PFP emulsions [Rapoport et al., Journal of Controlled Release 138: 268-76 (2009); Sheeran et al., Ultrasound Med Biol 37:1518-30 (2011)]. Spontaneous vaporization could be minimized by using a PFC with a higher boiling point or by minimizing the fraction of large PFP droplets, which are more likely to spontaneously vaporize [Sheeran et al., Ultrasound Med Biol 37:1518-30 (2011)]. Increasing the density/stiffness of the hydrogel may also establish less permissive conditions for spontaneous vaporization. Despite low levels of spontaneous vaporization, the exposure of the sham controls to ultrasound at day 5 caused a statistically significant increase in the amount of bFGF released on day 6. Thus, acoustic droplet-hydrogel composites can function as "on-demand" therapeutic agent delivery vehicles, with focused or unfocused ultrasound serving as the non-invasive stimulus for release.

Release of bFGF from 10 mg/mL fibrin composites was slower and cumulatively lower than that for 5 mg/mL gels. As described above, this may be attributed in part to a higher ADV threshold in the denser gels, which would reduce the number of vaporizable droplets and bFGF available for release upon exposure to a given ultrasound stimulus. Fibrin scaffolds exhibit density-dependent transport properties as well, as evidenced by a 2-3 fold reduction in effective diffusion coefficient for an increase in fibrin density from 2.5 mg/mL to 10 mg/mL [Ghajar et al., Biophys J 94: 1930-41 (2008)]. Fibrin can also bind bFGF [Sahni et al., J Biol Chem 273: 7554-9 (1998)], however, and since the number of binding sites increases with fibrin density, such diffusion-limiting interactions are expected to have a greater effect in the 10 mg/mL fibrin gels than in the lower density fibrin. In the context of therapeutic angiogenesis, retention of ADV-released bFGF within the hydrogel may be useful for establishing chemotactic gradients, and bFGF-fibrin complexes provide a higher proliferative stimulus to endothelial cells than bFGF alone [Sahni et al., Blood 107: 126-31 (2006)]. Alternatively, hydrogel scaffolds with lower protein affinities (e.g., polyethylene glycol) and/or more open pore structures may be used in place of fibrin to permit complete release of the payload carried by the acoustic droplets.

Under certain acoustic conditions, ultrasound has been shown to alter the structure and function of solubilized proteins [Tian et al., Ultrasonics Sonochemistry 11: 399-404

(2004); Marchioni et al., Ultrasonics 49: 569-76 (2009)]. FIG. 10 demonstrates that bFGF released by ADV is functionally bioactive. Computing the bioactivity of released bFGF relative to the amount of bFGF initially loaded into the emulsion is not straightforward with this dataset. However, based on the metabolic activities of cell cultures treated with known concentrations of bFGF and the measured concentrations of bFGF in the releasates, relative bioactivities of 13-48% are estimated, thus indicating that some bioactivity of the growth factor is lost upon either emulsion preparation and/or vaporization. If the reduction in bioactivity is due to effects caused by inertial cavitation, which is the rapid growth and violent collapse of a gas bubble, then ADV could be generated with a higher frequency transducer [Apfel et al., Ultrasound Med Biol 17:179-85 (1991)] or shorter pulses [Atchley et al., Ultrasonics 26:280-5 (1988)]. Since the acoustic threshold for ADV is inversely related to frequency [Kripfgans et al., IEEE Transactions on Ultrasonics, Ferroelectrics, and Frequency Control 49:726-38 (2002)], the use of a higher frequency transducer would permit the use of lower pressures while also having increased spatial resolution, though at the cost of penetration depth.

Viability of Co-Encapsulated Cells and Cell-Mediated Fibrinolysis

Droplet-hydrogel composites were prepared as described above except that either 1.25×10$^5$ HUVECs or cells of the mouse multipotent line C3H10T1/2, clone 8 (ATCC, catalog number CCL-226, Manassas, Va., USA) were co-encapsulated in each of the 0.5 mL gels along with 0, 1%, or 5% (v/v) double emulsion and 9.4 µg (5 mg/mL fibrin) or 18.8 µg (10 mg/mL fibrin) AF647-fibrinogen. These two cell populations were selected to assess any cell type-specific responses to ADV in the composites. In order to isolate the effects of ADV on cell viability, sham (i.e., without bFGF) emulsion was used for the composites. After polymerization, the gels were covered with 1 mL EGM for HUVECs or DMEM with penicillin/streptomycin and 10% FBS for C3H10T1/2 cells. A subset of the cell-gel constructs were then exposed to sham or ultrasound treatment as described above and placed in an incubator under standard cell culture conditions (37° C., 5% $CO_2$, 95% relative humidity). After 48 hours, the conditioned medium was collected and portions were assayed for AF647 fluorescence as an indicator of cell-mediated fibrinolysis, as described above. Some constructs were incubated for 2.5 hours in 10% (v/v) alamarBlue reagent, and the supernatants were assayed for fluorescence of the metabolized product as described above. Separate constructs were used for live/dead staining. The constructs were incubated for 1 hour at 37° C. with 5 µM 5-chloromethylfluorescein diacetate ("Live" stain: CMFDA, Invitrogen) and 10 µg/mL propidium iodide ("Dead" stain: PI, Invitrogen) diluted with DMEM with 10% FBS. The constructs were washed twice with PBS for 15 min at 37° C. and then mounted on microscope slides in coverwell imaging chambers. Images of CMFDA- and PI-labeled cells and AF647-labeled fibrin were captured with a SP5× microscope and a 10× objective.

Fibrinolysis with Plasmin

In order to assess the effects of droplets and ADV on enzymatic degradation of the fibrin hydrogel, experiments were conducted with cell-free constructs incubated with plasmin. Plasmin is an enzyme present in blood that degrades many blood plasma proteins, including fibrin clots. The degradation of fibrin is termed fibrinolysis. Gels were prepared as described above except with 15 µg AF647-fibrinogen added to each 0.5 mL gel. After polymerization, gels were treated with sham or ultrasound exposures and then overlaid with DMEM supplemented with 2.5 µg/mL human plasmin (Sigma-Aldrich) and incubated at 37° C. Aliquots of the DMEM were taken at various time points and analyzed for AF647 fluorescence ($\lambda_{ex}$: 620 nm/$\lambda_{em}$: 690 nm) with a Spectramax Gemini plate reader.

Results—Responses of Cells to Droplet-Hydrogel Composites

Figure 11A:
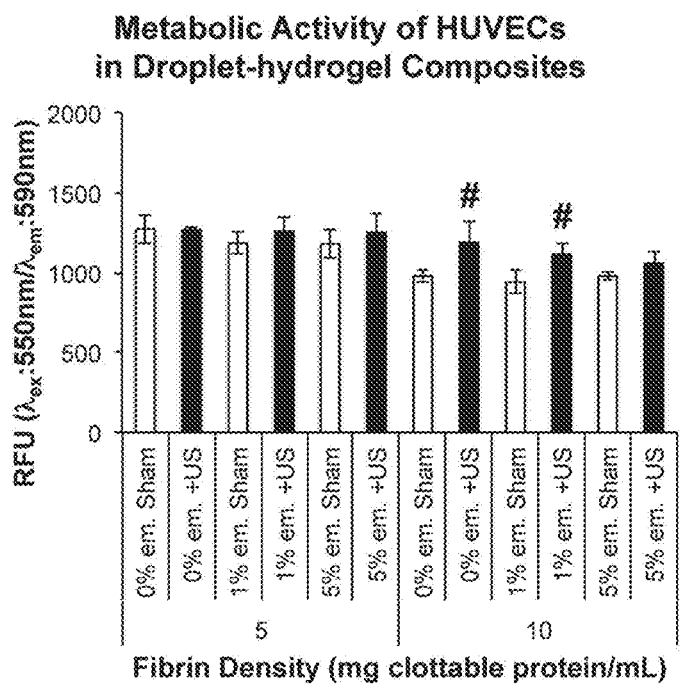
FIGS. 11A-C depicts the effects of ultrasound (US) exposure on HUVECs in droplet-hydrogel composites. The metabolic activity (A) and release of AF647 fibrinogen (B) from HUVEC-composites were measured 2 days after ADV. Data are shown as mean±standard deviation for n=5 (metabolic activity) and n=4 (release). # p<0.05 vs. sham control. CMFDA/PI labeling of HUVECs in 5 mg/mL fibrin constructs demonstrates proximity of viable cells to bubbles formed by ADV (C). The percentage of viable cells (mean±standard deviation; n=3) for each condition is given in the upper right. The right column displays zoomed in panels from the center column (denoted by the boxed regions). Arrows labeled "A" denote viable cells and arrows labeled "B" denote necrotic cells adjacent to the bubbles. Scale bars=200 µm.
Figure 11B:
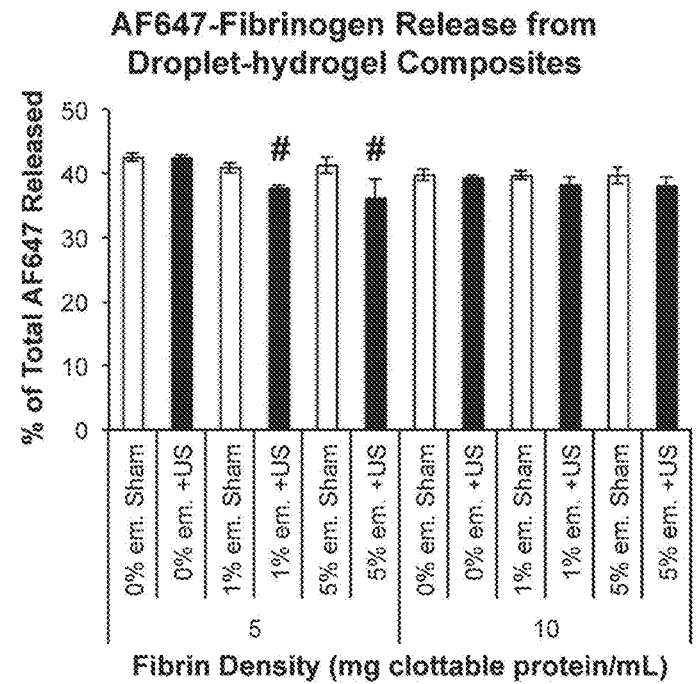
Figure 12:
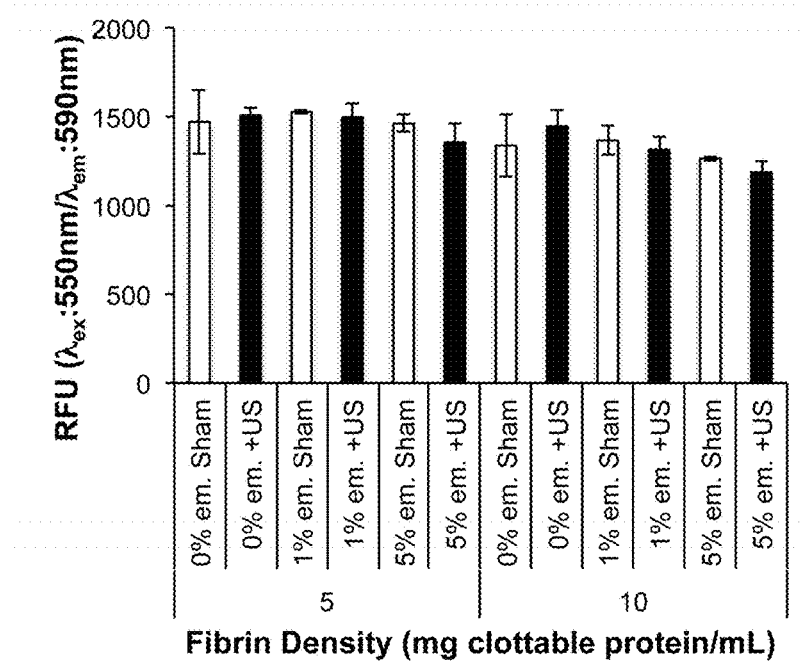
FIG. 12 shows the effects of ultrasound (US) exposure on C3H10T1/2 cells in droplet-hydrogel composites. The metabolic activity (A) and release of AF647 fibrinogen (B) from the cell-composites were measured 2 days after ADV. Data are shown as mean±standard deviation for n=5 (metabolic activity) and n=4 (release). $ p<0.05 vs. 0% emulsion sham or 1% emulsion sham. # p<0.05 vs. sham control.
Figure 12:
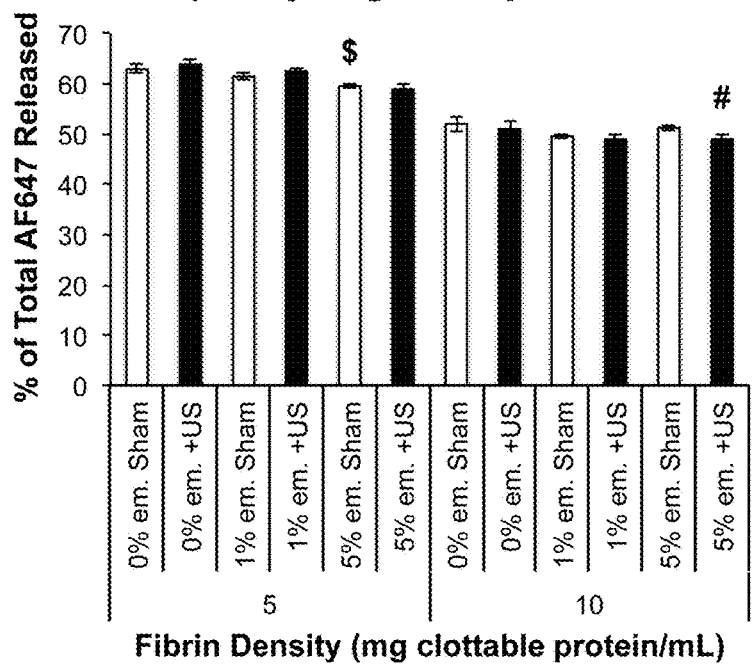

The viability of two cell types, primary HUVECs and the C3H10T1/2 mesenchymal progenitor line, cultured in sham- and ultrasound-treated droplet-hydrogel composites was evaluated quantitatively by metabolic assay and qualitatively by live/dead staining and confocal fluorescence microscopy. After 48 hours of in vitro culture, few differences in the metabolic activity between groups was detected. In HUVEC cultures there were modest but statistically significant increases in the metabolic activity of 10 mg/mL fibrin gels with 0% or 1% droplets treated with ultrasound compared to sham controls (FIG. 11A). These differences were not detected in analogous C3H10T1/2 cultures (FIG. 12A). The release of AF647 fibrinogen from gels containing either HUVECs or C3H10T1/2 cells is displayed in FIG. 11B and FIG. 12B, respectively. Several significant, but modest, differences were detected in the release of AF647 between various groups. For 5 mg/mL fibrin gels containing HUVECs, ultrasound treatment caused a 7.9% and 12.5% decrease in released fibrinogen concentration for scaffolds with 1% and 5% emulsion, respectively. Similarly, ultrasound caused decreases of 11.1% and 14.7% for the 5 mg/mL gels containing HUVECs with 1% and 5% emulsion, respectively, compared to 0% emulsion sham controls. In gels containing C3H10T1/2 cells, the largest difference in fibrinogen release was a 7.9% decrease in 5 mg/mL fibrin with 5% emulsion and ultrasound treatment compared to sham controls with 0% emulsion. No differences were detected for either cell type in 10 mg/mL fibrin gels. Thus, vaporization of droplets can reduce cell-mediated release of fibrin in vitro.

Figure 13:
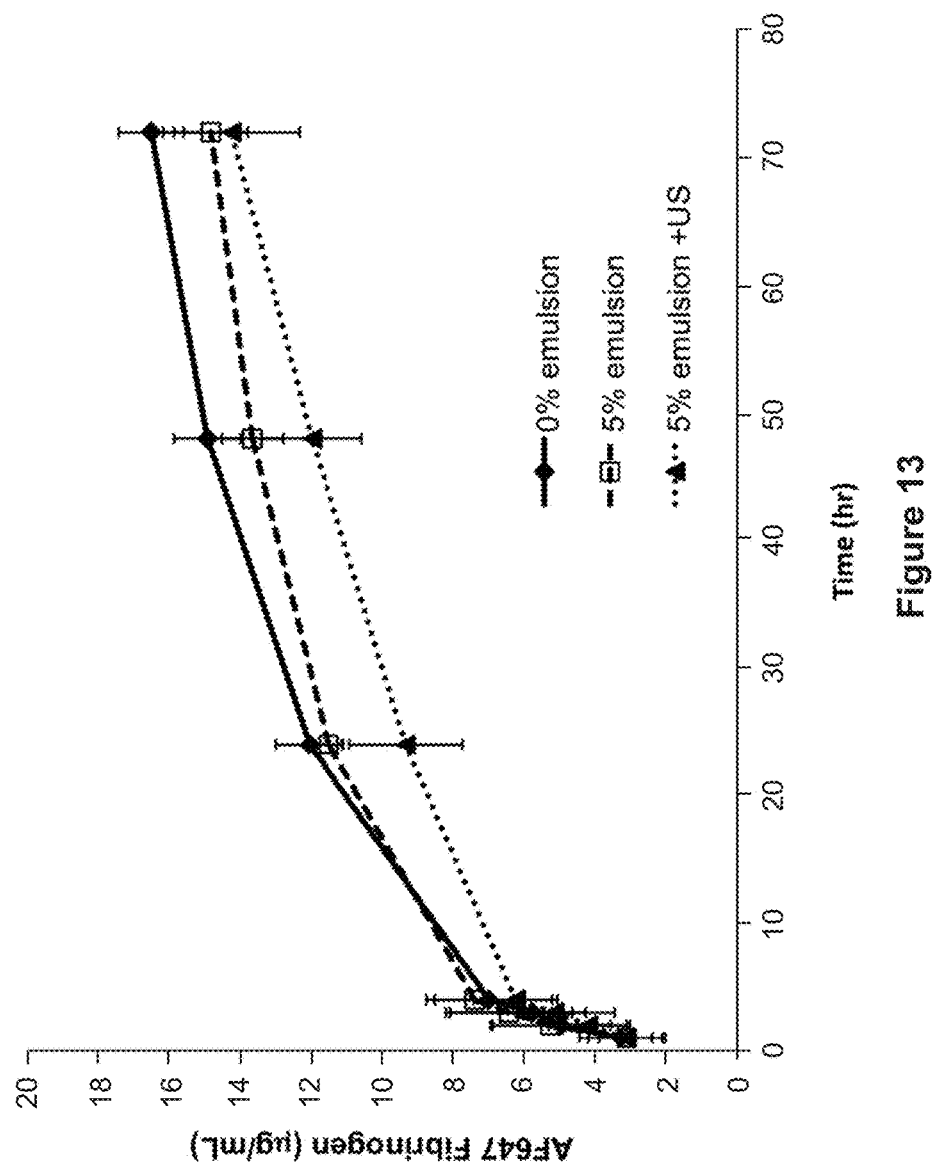
FIG. 13 shows the release of AF647 fibrinogen from 10 mg/mL fibrin gels incubated in plasmin. "+US" gels were exposed to ultrasound at time=0 hours. Data are shown as mean±standard deviation for n=3.

FIG. 13 shows representative release profiles of AF647 fibrinogen from cell-free gels incubated with plasmin. No statistically significant differences (p>0.05) were observed between gels without emulsion, with 1% or 5% emulsion, and with 1% or 5% emulsion and ultrasound treatment. These data indicate that neither the introduction of droplets nor the vaporization of droplets within the fibrin alters the susceptibility of the fibrin to degradation by exogenous proteases.

Figure 11C:
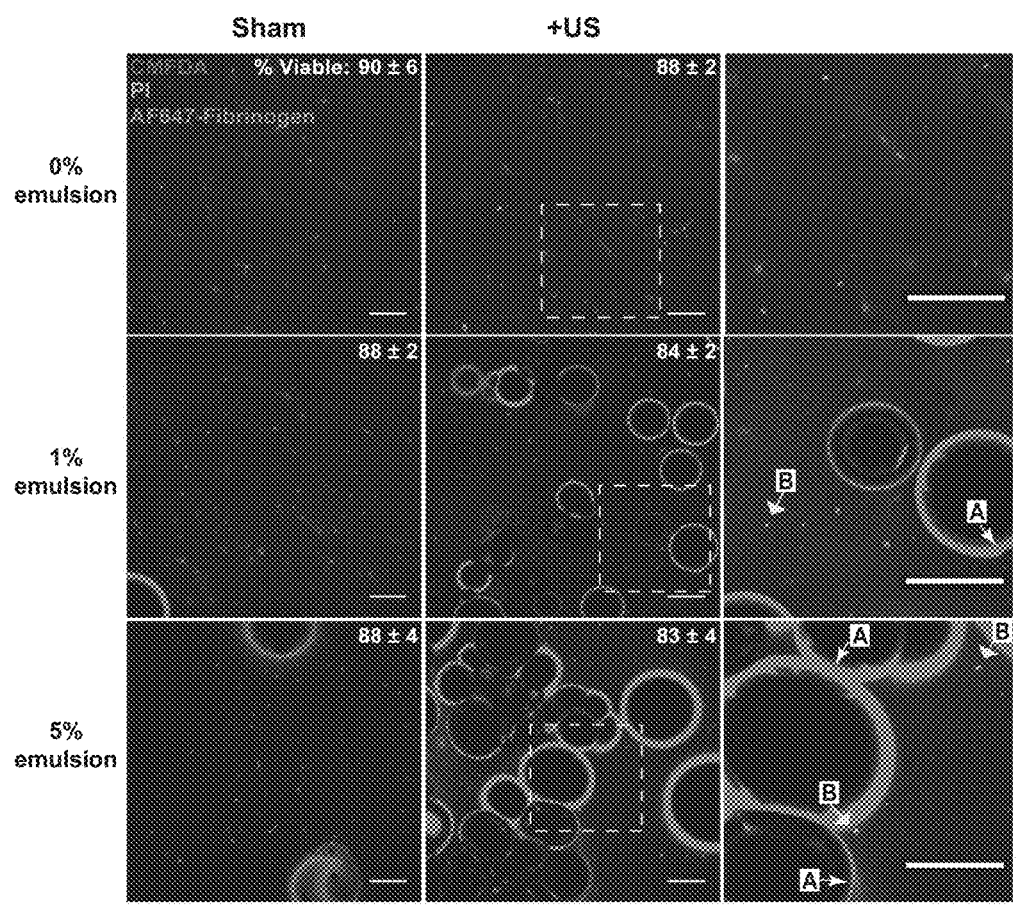

Confocal microscopy of live/dead-stained constructs confirmed the results of the metabolic assays. For HUVECs in 5 mg/mL fibrin composites, regardless of treatment group, 80-90% of cells were positive for CMFDA labeling (i.e., CMFDA$^+$) and negative for PI labeling (i.e., PI$^-$) after 48 hours of culture (FIG. 11C). Although there appeared to be modest decreases in CMFDA labeling in ultrasound-treated constructs compared to sham controls, these differences did not reach statistical significance. Similar results were obtained with 10 mg/mL fibrin gels and C3H10T1/2 populated constructs. Both CMFDA$^+$ and PI$^+$ cells were detected in close proximity to the margins of ADV-generated bubbles and pores. These results show that neither the droplet-hydrogel composites nor the ADV process generated statistically significant differences in cell viability.

A previous study demonstrated that ADV occurring adjacent to adherent cells, within culture medium, caused cell detachment and potentially cell death [Fabiilli et al., Ultrasound Med Biol 36: 1364-75 (2010), incorporated by reference herein in its entirety]. This is likely due to the elevated fluid velocities and shear forces generated during the conversion of the liquid PFC droplets into microbubbles [Kripfgans et al., J Acoust Soc Am 116: 272-81 (2004), incorporated by reference herein in its entirety]. In contrast, ADV of emulsion contained within the droplet-hydrogel composite did not affect viability of two different cell types and only caused slight reductions in cell-mediated release of AF647-labeled fibrin in vitro at a density of 5 mg/mL. Thus, fibrin gels inhibit cytotoxic effects stemming from ADV, with the inhibition related to gel density. For some conditions, ultrasound stimulated the metabolic activity of HUVECs within the scaffolds, which is consistent with previous findings [Doan et al., J Oral Maxil Surg 57: 409-19 (1999); Altland et al., J Thromb Haemost 2: 637-43 (2004)]. These results suggest that the acoustic droplet-hydrogel composites are also suitable carriers for populations of cells that can participate in regenerative processes such as angiogenesis.

Statistics

Data are expressed as the mean±standard deviation of 3-5 samples per experimental group. ELISA and fluorescence assays were performed in duplicate or triplicate and averaged for each sample. Analysis of variance (ANOVA) was used to establish the significance between experimental groups. The Tukey-Kramer method, evaluated in MATLAB (The MathWorks Inc., Natick, Mass., USA), was used to determine statistically significant differences between multiple groups, with differences deemed significant for $p<0.05$.

Example 4

The objectives of the following example were to demonstrate in vivo selective release from acoustic droplet-hydrogel composites, as well as to assess implantation method (i.e., subcutaneous injection versus implantation of pre-cast implant).

Methods

Preparation and Implantation of Fibrin Scaffolds

All animal protocols were approved by the University Committee on Use and Care of Animals at the University of Michigan. Sonosensitive double emulsions were prepared containing fluorescein sodium in the W1 phase and different ratios of perfluoropentane:perfluorohexane (Table 3). A total of 10 fibrin implants (total volume: 0.5 mL) were prepared by combining 5% (v/v) emulsion with fibrinogen, Alexa Fluor 647 labeled fibrinogen, Dulbecco's Modified Eagle Medium (DMEM), and thrombin. Prior to implantation of the fibrin scaffolds, C57BL/6 mice (n=5) were anesthetized using isoflurane (5% for induction and 1-2% for maintenance) and the hair on each mouse's back was removed using clippers and depilatory cream to aid in ultrasound coupling. For half of the implants, the polymerizable mixture was injected subcutaneously beneath the dorsal skin. For the other implants, the polymerizable mixture was pipetted into a 24 well culture dish (Bioflex, Flexcell International Co., Hillsborough, N.C., USA) and allowed to polymerize for 30 minutes. The pre-cast implant was then removed from the plate and implanted into subcutaneous pouches beneath the dorsal skin. Each mouse received a total of two implants. Skin incisions related to the pre-cast gel implantation were sealed using surgical glue (Surgi-Lock 2oc, Meridian Animal Health, Omaha, Nebr., USA).

TABLE 3

Experimental groups for the in vivo study. All implants contained 10 mg/mL fibrin and 5% (v/v) emulsion, except for the sham implants in mouse #265 (i.e., 0% emulsion).

| Mouse # | Scaffold | Perfluorocarbon in Emulsion |
|---|---|---|
| 265 | Implanted (n = 1), Injected (n = 1) | none |
| 861 | Injected (n = 2) | 90% $C_5F_{12}$ + 10% $C_6F_{14}$ |
| 870 | Injected (n = 2) | 70% $C_5F_{12}$ + 30% $C_6F_{14}$ |
| 213 | Implanted (n = 2) | 90% $C_5F_{12}$ + 10% $C_6F_{14}$ |
| 834 | Implanted (n = 2) | 70% $C_5F_{12}$ + 30% $C_6F_{14}$ |

Ultrasound Exposure

Thirty minutes following scaffold implantation the anesthetized mouse was placed in a lateral recumbent position on top of a heating pad. One of the implanted scaffold was then covered in ultrasound gel. Morphology of the implanted scaffold was assessed using B-mode ultrasound (Zonare z.one). A 2.5 MHz single element transducer (H-108, Sonic Concepts, Bothell, Wash., USA), driven in a pulsed mode (10 cycles, 10 ms pulse repetition period) using a 55 dB radiofrequency amplifier (A-300, ENI, Rochester, N.Y., USA), was used to generate acoustic droplet vaporization (ADV) within the implanted scaffold. For each mouse, one scaffold was exposed to ultrasound (i.e., ADV) whereas the other served as a sham control (i.e., without ADV). Following ultrasound exposure, each mouse was allowed to recover.

In Vivo Fluorescence Imaging

Implants were imaged using an in vivo imaging system (IVIS Spectrum, PerkinElmer, Waltham, Mass., USA) at 1 and 4 days following implantation. At each time point, the fluorescence signals from fluorescein (excitation 465 nm, emission 520 nm) and AF647 fibrinogen (excitation 640 nm, emission 680 nm) were spatially mapped.

Results

Figure 14:
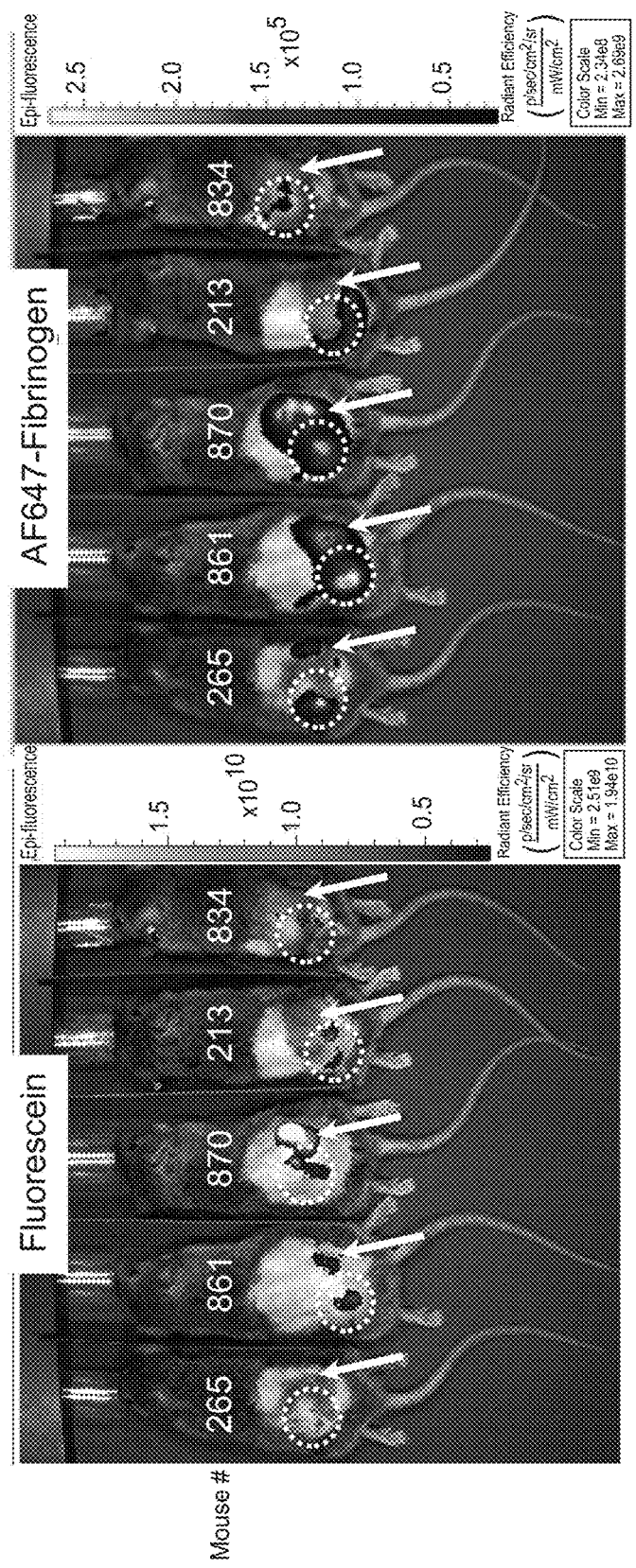
FIG. 14 shows fluorescence images of mice containing subcutaneous fibrin implants. The left and right images display the fluorescence signal from fluorescein and AF647-fibrinogen, respectively, at 1 day post implantation. Implants exposed to ultrasound are denoted by a dashed circle whereas control scaffolds (i.e., not exposed to ultrasound) are denoted by a white arrow.
Figure 15:
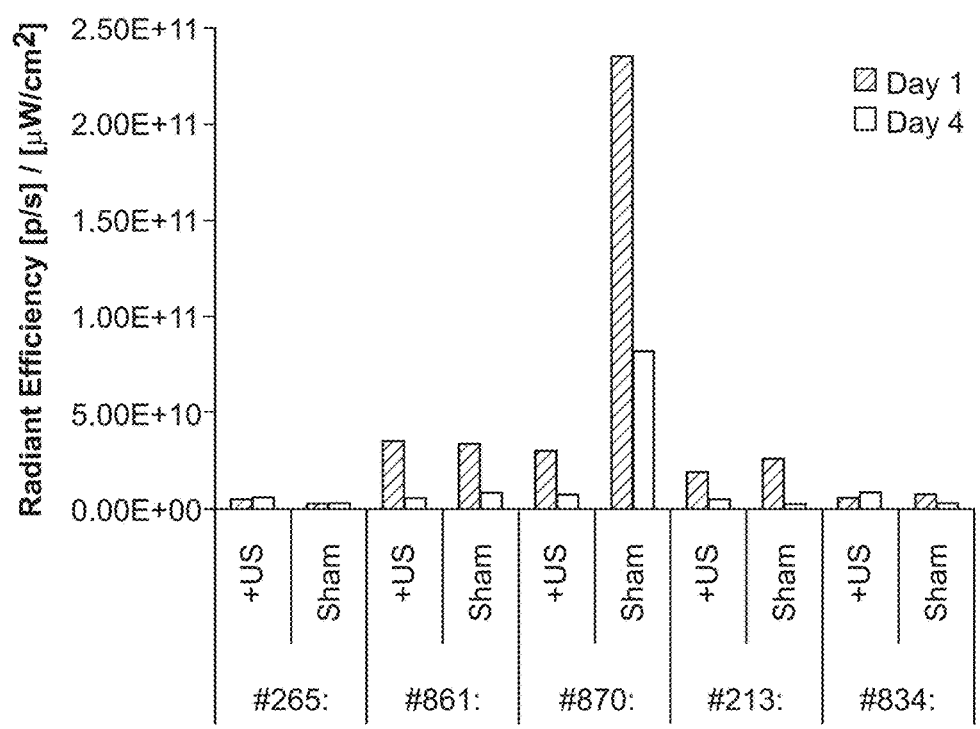
FIG. 15 depicts the quantification of the fluorescein retained within the implants. Scaffolds exposed to ultrasound to generate ADV are denoted by "+US." Signal in mouse #213 and mouse #834 was largely obscured by the dark regions of hair/skin near the implantation sites. Low signal was expected in mouse #265 since it received sham (i.e., without emulsion) implants.

Based on B-mode ultrasound, all scaffold appeared homogenous regardless of implantation method. FIG. 14 displays in vivo fluorescence images of the various experimental groups. FIG. 15 displays the quantified fluorescein signal measured at 1 and 4 days post implantation. Based on mouse #870, ADV caused a decrease in the fluorescein signal, compared to sham conditions, which is indicative of release caused by ADV. In both test and sham groups, the fluorescein signal decreased from day 1 to day 4. Higher fluorescein levels were measured in mouse #870 versus mouse #861, which is indicative of the more thermally-stable emulsion formulation used in mouse #870. No trends were observed with the AF647-fibrinogen signal during days 1 and 4.

CONCLUSIONS

Example 4 showed that either implantation method (i.e., subcutaneous injection versus implantation of pre-cast implant) is suitable, with direct injection being the easier method since it does not require skin incisions. In addition, ADV was shown to increase the amount of fluorescein released from the implanted scaffold.

The Example further showed that increasing the ratio of perfluorohexane to perfluoropentane increases the thermal stability of the emulsion, thus minimizing non-selective release. Finally, the Example suggested the use of BALB/c mice in future experiments in order to minimize fluorescence signal obscuration caused by dark skin/hair.

Each of the references cited herein is incorporated by reference in its entirety, or as relevant in view of the context of the citation.

From the disclosure provided herein it will be appreciated that, although specific embodiments of the invention have been described herein for purposes of illustration, various modifications may be made without deviating from the spirit and scope of the invention.

What is claimed is:

1. A method of delivering an effective amount of a therapeutic agent to an individual in need thereof comprising administering to the individual a device comprising:
   (a) a hydrogel scaffold having a density of polymer within the hydrogel scaffold of about 1 mg/mL to about 50 mg/mL; and
   (b) an emulsion comprising a first population of perfluorocarbon (PFC) droplets comprising a first therapeutic agent in the interior thereof, said first population of PFC droplets being within the hydrogel scaffold and having the property of vaporizing at a first ultrasound frequency and/or acoustic pressure threshold; the device further comprising
   a second population of PFC droplets comprising a second therapeutic agent in the interior thereof, said second population of PFC droplets being within the hydrogel scaffold and having the property of vaporizing at a second ultrasound frequency and/or acoustic pressure threshold that is different than the first ultrasound frequency and/or acoustic pressure threshold, and
   exposing the hydrogel scaffold to the first ultrasound frequency and/or acoustic pressure threshold to deliver the first therapeutic agent,
   wherein the concentration of the first population of PFC droplets is sufficient to result in acoustic shadowing upon exposure of the first population of PFC droplets to ultrasound.

2. The method of claim 1, wherein the device further comprises a progenitor cell.

3. The method of claim 2 wherein the progenitor cell is a fibroblast, a chondrocyte, an osteoblast, a skeletal myocyte, a cardiac myocyte, a mesenchymal progenitor cell, a hematopoietic progenitor cell, a satellite cell, a neural progenitor cell, a pancreatic progenitor cell, a blast cell or a combination thereof.

4. The method of claim 1 wherein the emulsion is a double emulsion comprising a primary emulsion and a secondary emulsion.

5. The method of claim 4 wherein the primary emulsion comprises water-in-PFC, and the secondary emulsion comprises water-in-PFC-in-water.

6. The method of claim 5, wherein the device further comprises a surfactant.

7. The method of claim 6, wherein a first surfactant stabilizing the primary emulsion is a triblock copolymer, and a second surfactant stabilizing the secondary emulsion is an aqueous soluble surfactant.

8. The method of claim 7 wherein the triblock copolymer comprises a perfluoroether and polyethylene glycol.

9. The method of claim 7 wherein the aqueous soluble surfactant is selected from the group consisting of a protein, a lipid, an ionic copolymer and a non-ionic copolymer.

10. The method of claim 1 wherein initial pore size of the hydrogel scaffold is at least about 100 nanometers (nm).

11. The method of claim 1 wherein vaporization of the PFC droplet results in a final pore size within the hydrogel scaffold of at least about 40 µm and up to about 5 millimeters (mm).

12. The method of claim 1, wherein the density of the hydrogel scaffold is between about 1 mg/mL to about 20 mg/ml fibrinogen.

13. The method of claim 1 wherein the device is implantable.

14. The method of claim 1 wherein the device is topical.

15. The method of claim 1 wherein the first and/or second therapeutic agent is selected from the group consisting of a polypeptide, a peptide, a polynucleotide, a viral particle, a gas, a contrast agent and a small molecule.

16. The method of claim 1 wherein release of the first and/or second therapeutic agent is controlled spatially.

17. The method of claim 1 wherein release of the first and/or second therapeutic agent is controlled temporally.

18. The method of claim 1 wherein the first therapeutic agent and the second therapeutic agent are different.

19. The method of claim 1 wherein the device is administered to the individual by implantation.

20. The method of claim 19 wherein the implantation is subcutaneous or intramuscular.

21. The method of claim 1 wherein the volume fraction of the hydrogel scaffold that is taken up by all PFC droplets is from about 1% to about 10%, wherein the volume fraction of the first population of PFC droplets is at least 0.1%.

22. The method of claim 21 wherein the average diameter of the PFC droplets is from about 1 µm to about 100 µm.

23. The method of claim 21 wherein the average diameter of the PFC droplets is from about 0.1 µm to about 50 µm.

24. The method of claim 22 wherein the average diameter of the PFC droplets is about 5 µm, about 10 µm, about 15 µm, about 20 µm, or about 50 µm.

25. The method of claim 1, further comprising exposing the hydrogel scaffold to the second ultrasound frequency and/or acoustic pressure threshold to deliver the second therapeutic agent.

* * * * *